(12) United States Patent
Gonzales et al.

(10) Patent No.: US 8,979,875 B2
(45) Date of Patent: *Mar. 17, 2015

(54) METHODS AND SYSTEMS FOR MEDIALIZING A TURBINATE

(75) Inventors: Donald A. Gonzales, San Antonio, TX (US); Fred B. Dinger, III, San Antonio, TX (US); Gabriele G. Niederauer, San Antonio, TX (US); Jeffrey S. Wrana, San Antonio, TX (US)

(73) Assignee: ArthroCare Corporation, Austin, TX (US)

( * ) Notice: Subject to any disclaimer, the term of this patent is extended or adjusted under 35 U.S.C. 154(b) by 159 days.

This patent is subject to a terminal disclaimer.

(21) Appl. No.: 13/474,121

(22) Filed: May 17, 2012

(65) Prior Publication Data

US 2012/0232584 A1  Sep. 13, 2012

Related U.S. Application Data

(63) Continuation of application No. 12/561,707, filed on Sep. 17, 2009, now Pat. No. 8,192,450.

(60) Provisional application No. 61/097,741, filed on Sep. 17, 2008.

(51) Int. Cl.
*A61B 17/08* (2006.01)
*A61B 17/24* (2006.01)
*A61B 17/04* (2006.01)
*A61B 17/064* (2006.01)
*A61B 17/068* (2006.01)

(52) U.S. Cl.
CPC .............. *A61B 17/24* (2013.01); *A61B 17/0401* (2013.01); *A61B 17/064* (2013.01); *A61B 17/0483* (2013.01); *A61B 17/068* (2013.01); *A61B 2017/0409* (2013.01); *A61B 2017/0417* (2013.01); *A61B 2017/0461* (2013.01); *A61B 2017/0641* (2013.01); *A61B 2017/0647* (2013.01)
USPC .............. 606/151; 606/213; 606/215; 623/10

(58) Field of Classification Search
None
See application file for complete search history.

(56) References Cited

U.S. PATENT DOCUMENTS 4,259,959 A    4/1981   Walker ........................... 606/221
4,696,300 A    9/1987   Anderson ...................... 606/219

(Continued)

FOREIGN PATENT DOCUMENTS

EP       1 297 788       4/2003
WO       WO 03/080003    1/2003
WO       WO 03/057274    7/2003

OTHER PUBLICATIONS

Orlandi and Kennedy, "Revision endoscopic frontal sinus surgery," *Otolaryngologic Clinics of North America*, 34(1): 77-90, Feb. 2001.

(Continued)

*Primary Examiner* — Elizabeth Houston
*Assistant Examiner* — Todd J Scherbel
(74) *Attorney, Agent, or Firm* — Norman F. Hainer, Jr.

(57) ABSTRACT

Methods and systems for medializing a turbinate. Exemplary embodiments comprise methods and systems for repositioning a turbinate proximal to a septum. Certain embodiments comprise an implant and a flexible member coupled to the implant. Embodiments may also comprise an insertion device to install the implant in a desired location.

11 Claims, 29 Drawing Sheets

(56) References Cited

U.S. PATENT DOCUMENTS

| | | | |
|---|---|---|---|
| 4,873,976 A | 10/1989 | Schreiber | 606/213 |
| 4,884,572 A | 12/1989 | Bays et al. | 606/139 |
| 4,895,148 A | 1/1990 | Bays et al. | 606/213 |
| 4,917,114 A | 4/1990 | Green et al. | 227/179.1 |
| 4,924,865 A | 5/1990 | Bays et al. | 606/77 |
| 4,932,960 A | 6/1990 | Green et al. | 606/220 |
| 4,976,715 A | 12/1990 | Bays et al. | 606/77 |
| 4,991,764 A | 2/1991 | Mericle | 227/178.1 |
| 4,994,073 A | 2/1991 | Green | 606/220 |
| 5,040,715 A | 8/1991 | Green et al. | 227/176.1 |
| 5,059,206 A | 10/1991 | Winters | 606/213 |
| 5,089,009 A | 2/1992 | Green | 606/219 |
| 5,094,233 A | 3/1992 | Brennan | 602/6 |
| 5,108,422 A | 4/1992 | Green et al. | 606/219 |
| 5,116,349 A | 5/1992 | Aranyi | 227/181.1 |
| 5,125,553 A | 6/1992 | Oddsen et al. | 227/175.1 |
| 5,129,906 A | 7/1992 | Ross et al. | 606/77 |
| 5,203,784 A | 4/1993 | Ross et al. | 606/104 |
| 5,246,441 A | 9/1993 | Ross et al. | 606/53 |
| 5,246,455 A | 9/1993 | Shikani | 623/10 |
| 5,269,783 A | 12/1993 | Sander | 606/148 |
| 5,293,881 A | 3/1994 | Green et al. | 128/898 |
| 5,336,163 A | 8/1994 | DeMane et al. | 602/46 |
| 5,342,376 A | 8/1994 | Ruff | 606/151 |
| 5,344,060 A | 9/1994 | Gravener et al. | 227/180.1 |
| 5,350,396 A | 9/1994 | Eliachar | 606/199 |
| 5,351,871 A | 10/1994 | Bauer | 227/177.1 |
| 5,361,782 A | 11/1994 | Bauer | 128/898 |
| 5,366,134 A | 11/1994 | Green et al. | 227/176.1 |
| 5,366,459 A | 11/1994 | Yoon | 606/151 |
| 5,370,294 A | 12/1994 | Bauer | 227/177.1 |
| 5,374,268 A | 12/1994 | Sander | 606/148 |
| 5,417,691 A | 5/1995 | Hayhurst | 606/232 |
| 5,423,858 A | 6/1995 | Bolanos et al. | 606/220 |
| 5,425,747 A | 6/1995 | Brotz | 606/228 |
| 5,478,354 A | 12/1995 | Tovey et al. | 606/219 |
| 5,527,318 A | 6/1996 | McGarry | 606/139 |
| 5,535,935 A | 7/1996 | Vidal et al. | 227/175.2 |
| 5,540,240 A | 7/1996 | Bauer | 128/898 |
| 5,569,272 A | 10/1996 | Reed et al. | 606/151 |
| 5,584,859 A | 12/1996 | Brotz | 606/228 |
| 5,593,423 A | 1/1997 | Person et al. | 606/219 |
| 5,599,284 A | 2/1997 | Shea | 602/17 |
| 5,601,558 A | 2/1997 | Torrie et al. | 606/326 |
| 5,628,751 A | 5/1997 | Sander et al. | 606/104 |
| 5,643,319 A | 7/1997 | Green et al. | 606/218 |
| 5,653,373 A | 8/1997 | Green et al. | 227/175.1 |
| 5,655,698 A | 8/1997 | Yoon | 227/176.1 |
| 5,658,312 A | 8/1997 | Green et al. | 606/219 |
| 5,713,839 A | 2/1998 | Shea | 602/217 |
| 5,716,405 A | 2/1998 | Mittelman | 623/10 |
| 5,720,753 A | 2/1998 | Sander et al. | 606/104 |
| 5,782,396 A | 7/1998 | Mastri et al. | 227/175.3 |
| 5,807,302 A | 9/1998 | Wandel | 604/8 |
| 5,810,240 A | 9/1998 | Robertson | 227/175.2 |
| 5,817,109 A | 10/1998 | McGarry et al. | 606/143 |
| 5,827,298 A | 10/1998 | Hart et al. | 606/139 |
| 5,843,084 A | 12/1998 | Hart et al. | 606/77 |
| 5,915,615 A | 6/1999 | Bauer | 227/177.1 |
| 5,964,394 A | 10/1999 | Robertson | 227/176.1 |
| 5,976,127 A | 11/1999 | Lax | 606/32 |
| 5,980,524 A | 11/1999 | Justin et al. | 606/75 |
| 5,984,927 A | 11/1999 | Wenstrom, Jr. et al. | 606/329 |
| 6,017,346 A | 1/2000 | Grotz | 606/323 |
| 6,131,790 A | 10/2000 | Piraka | 227/176.1 |
| 6,187,009 B1 | 2/2001 | Herzog et al. | 606/75 |
| 6,190,401 B1 | 2/2001 | Green et al. | 606/224 |
| 6,241,747 B1 | 6/2001 | Ruff | 606/216 |
| 6,264,086 B1 | 7/2001 | McGuckin, Jr. | 227/180.1 |
| 6,270,517 B1 | 8/2001 | Brotz | 606/228 |
| 6,283,121 B1 | 9/2001 | Fukutomi | 128/205.13 |
| 6,322,563 B1 | 11/2001 | Cummings et al. | 606/916 |
| 6,406,479 B1 | 6/2002 | Justin et al. | 606/104 |
| 6,446,854 B1 | 9/2002 | Remiszewski et al. | 227/175.1 |
| 6,478,804 B2 | 11/2002 | Vargas | 606/153 |
| 6,485,503 B2 | 11/2002 | Jacobs et al. | 606/215 |
| 6,517,564 B1 | 2/2003 | Grafton et al. | 606/213 |
| 6,551,343 B1 | 4/2003 | Tormala et al. | 606/213 |
| 6,554,852 B1 | 4/2003 | Oberlander | 606/232 |
| 6,565,581 B1 | 5/2003 | Spence et al. | 606/153 |
| 6,629,988 B2 | 10/2003 | Weadock | 606/219 |
| 6,645,226 B1 | 11/2003 | Jacobs et al. | 606/215 |
| 6,666,872 B2 | 12/2003 | Barreiro et al. | 606/142 |
| 6,692,499 B2 | 2/2004 | Tormala et al. | 606/213 |
| 6,726,705 B2 | 4/2004 | Peterson et al. | 606/216 |
| 6,773,440 B2 | 8/2004 | Gannoe et al. | 606/142 |
| 6,893,452 B2 | 5/2005 | Jacobs | 606/215 |
| 2,525,183 A1 | 10/2005 | Robison | 606/196 |
| 6,966,919 B2 | 11/2005 | Sixto, Jr. et al. | 606/153 |
| 6,981,983 B1 | 1/2006 | Rosenblatt et al. | 606/216 |
| 6,991,643 B2 | 1/2006 | Saadat | 606/221 |
| 7,014,638 B2 | 3/2006 | Michelson | 606/1 |
| 7,028,878 B2 | 4/2006 | Bauer | 227/175.1 |
| 7,033,378 B2 | 4/2006 | Smith et al. | 606/220 |
| 7,105,010 B2 | 9/2006 | Hart et al. | 606/213 |
| 7,156,862 B2 | 1/2007 | Jacobs et al. | 606/215 |
| 7,169,163 B2 | 1/2007 | Becker | 606/196 |
| 7,172,615 B2 | 2/2007 | Morriss et al. | 606/215 |
| 7,211,088 B2 | 5/2007 | Grafton et al. | 606/77 |
| 7,220,272 B2 | 5/2007 | Weadock | 606/219 |
| 7,226,468 B2 | 6/2007 | Ruff | 606/216 |
| 7,226,469 B2 | 6/2007 | Benavitz et al. | 606/232 |
| 7,361,168 B2 | 4/2008 | Makower et al. | 604/509 |
| 7,410,480 B2 | 8/2008 | Muni et al. | 604/509 |
| 7,413,570 B2 | 8/2008 | Zamierowski | 606/215 |
| 7,427,292 B2 | 9/2008 | Sachs | 623/10 |
| 7,431,730 B2 | 10/2008 | Viola | 606/219 |
| 7,736,377 B1 | 6/2010 | Anson et al. | 606/219 |
| 8,192,450 B2* | 6/2012 | Gonzales et al. | 606/151 |
| 8,235,050 B2* | 8/2012 | Gonzales | 128/848 |
| 2002/0022861 A1 | 2/2002 | Jacobs et al. | 606/216 |
| 2002/0077661 A1 | 6/2002 | Saadat | 606/221 |
| 2002/0111603 A1 | 8/2002 | Cheikn | 424/426 |
| 2003/0022006 A1 | 1/2003 | Phillips et al. | 623/1.36 |
| 2003/0045902 A1 | 3/2003 | Weadock | 606/219 |
| 2003/0187381 A1 | 10/2003 | Greenawalt et al. | 604/11 |
| 2004/0010276 A1* | 1/2004 | Jacobs et al. | 606/153 |
| 2004/0064150 A1 | 4/2004 | Becker | 606/196 |
| 2005/0113850 A1 | 5/2005 | Tagge | 606/151 |
| 2005/0192628 A1 | 9/2005 | Viola | 606/219 |
| 2005/0222610 A1 | 10/2005 | Melker | 606/205 |
| 2005/0273138 A1 | 12/2005 | To et al. | 606/21 |
| 2006/0276817 A1 | 12/2006 | Vassallo et al. | 623/10 |
| 2007/0005094 A1 | 1/2007 | Eaton et al. | 604/19 |
| 2007/0021777 A1 | 1/2007 | Fowler et al. | 606/205 |
| 2007/0073269 A1 | 3/2007 | Becker | 604/509 |
| 2007/0073336 A1 | 3/2007 | Hart et al. | 606/213 |
| 2007/0293946 A1* | 12/2007 | Gonzales et al. | 623/10 |
| 2008/0154237 A1 | 6/2008 | Chang et al. | 604/514 |
| 2008/0172033 A1 | 7/2008 | Keith et al. | 604/506 |
| 2009/0084389 A1* | 4/2009 | Gonzales | 128/848 |
| 2009/0149882 A1 | 6/2009 | Tagge | 606/213 |
| 2009/0312745 A1 | 12/2009 | Goldfarb et al. | 604/514 |
| 2010/0076485 A1* | 3/2010 | Gonzales et al. | 606/213 |
| 2011/0022172 A1 | 1/2011 | Gonzales et al. | 623/10 |
| 2012/0232584 A1* | 9/2012 | Gonzales et al. | 606/213 |
| 2013/0032155 A1* | 2/2013 | Gonzales | 128/848 |

OTHER PUBLICATIONS

PCT International Search Report and Written Opinion, issued in International Application No. PCT/US2009/057288, dated Nov. 20, 2009.

"Novel Device for Simplifying Septoplasty Procedures," University of Florida Office of Technology Licensing, www.otl.ufl.edu.

Heublein et al., "Biocorrosion of magnesium alloys: a new principle in cardiovascular implant technology?" *Heart*, 89:651-656, 2003.

Melker, "Method and Apparatus for Performing Septal Surgeries," U.S. Appl. No. 60/553,501, filed Mar. 16, 2004.

Supplementary European Search Report, issued in European Application No. 07762117, dated Nov. 25, 2009.

Office Communication, issued in European Patent Application No. 07 762 117.5, dated Nov. 24, 2010.

(56) References Cited

OTHER PUBLICATIONS

Office Communication issued in U.S. Appl. No. 11/747,442, dated Jun. 10, 2009.
Amendment and Response to Office Action dated Jun. 10, 2009, issued Oct. 7, 2009 is U.S. Appl. No. 11/747,442.
Office Communication issued in U.S. Appl. No. 11/747,442 dated Jan. 4, 2010.
Request for Continued Examination in U.S. Appl. No. 11/747,442 dated Jul. 2, 2010.
Office Communication in U.S. Appl. No. 11/747,442 issued Aug. 18, 2010.
Amendment and Response to Office Action Dated Aug. 18, 2010, issued Dec. 14, 2010 in U.S. Appl. No. 11/747,442.
Office Communication in U.S. Appl. No. 11/747,442 issued Feb. 24, 2011.
Request for Continued Examination in U.S. Appl. No. 11/747,442, filed Jun. 23, 2011.
International Preliminary Report on Patentability in PCT/US2009/057288 issued Mar. 31, 2011.
PCT International Preliminary Report on Patentability for PCT/US2012/053420 7pgs, Mar. 20, 2014.

* cited by examiner

METHODS AND SYSTEMS FOR MEDIALIZING A TURBINATE

CROSS-REFERENCE TO RELATED APPLICATIONS

This application is a continuation of U.S. patent application Ser. No. 12/561,707 filed Sep. 17, 2009, now U.S. Pat. No. 8,192,450, which claims priority to U.S. Provisional Application No. 61/097,741 filed on Sep. 17, 2008. The entire text of each of the above-referenced disclosures is specifically incorporated herein by reference without disclaimer.

BACKGROUND OF THE INVENTION

Sinusitis is a progression of inflammation, stasis, infection, and continued inflammation. Typically, the beginning of all sinus infections is either allergy or viral infection. Both of these conditions lead to swelling of the sinus and nasal mucosa that when severe enough, causes the small holes, called ostia, of the sinuses to close. Once the ostia are closed, the environment inside the sinuses becomes conducive to bacterial growth. The way this typically occurs is that once the ostia are shut, the oxygen content of the sinus drops and the fluid inside the sinus is unable to escape which leads to further inflammation. The reduced oxygen content and inflammation disrupts the ability of the cilia of the cells of the sinus to operate properly which leads to further stasis.

The typical patient that is seen by the otolaryngologist is started on antibiotics. Usually the antibiotic course can be as long as six weeks to eradicate the bacteria and bring the sinuses back to normal. For those patients in whom antibiotics do not relieve the problem, the primary alternative is surgery. Although sinus and nasal surgeries are now common with 500,000 to 700,000 of such surgeries being performed annually in the U.S., these surgeries are typically both destructive and permanent. Around 10% of patients who undergo sinus surgery have scarring that leads to continued sinus problems which frequently require revision surgery.

One frequent problem is postoperative adhesions. These adhesions can occur between the middle turbinate and the adjacent nasal areas. One particular problem is the adhesion of the middle turbinate to the lateral nasal wall. Some surgeons have proposed removing the lower half of the middle turbinate to avoid this problem. This procedure, however, has its own problems (e.g., crust formation, nasal hygiene issues).

Other solutions that have been suggested include placing a suture through the middle turbinate on one side of the nose, through the nasal septum, and then through the middle turbinate on the other side before the suture is tied off. Such a suture draws the middle turbinates medially and prevents the formation of adhesions between the middle turbinate and the lateral nasal wall. However, this suture is difficult and time-consuming to place and requires the puncturing of three separate structures in the nose. This can lead to discomfort for the patient, bleeding, infection, and other complications.

Another solution surgeons have proposed is the use of various packing materials and splints. The use of these materials and devices however leads to the formation of scar tissue, which is undesirable and can lead to airway obstruction and infection. The adhesion of the middle turbinate to adjacent structures in the nose remains a problem in nasal and sinus surgery.

Given this serious and common complication of sinus surgery, there remains a need in the art for preventing the formation of adhesions between the middle turbinate and adjacent nasal structures, particularly the lateral nasal wall. The desired solution preferably limits or eliminates the complications of the other proposals which have been used including infection, scar tissue formation, adhesions, bleeding, and patient discomfort.

SUMMARY OF THE INVENTION

Embodiments of the present disclosure provide methods and systems for reducing the adhesions formed in a patient's nasal cavity following a sinus or nasal procedure. In particular, embodiments reduce the formation of adhesions between the lateral nasal wall and the middle turbinate by directing the middle turbinate toward the nasal septum. This system pulls the middle turbinate medially to avoid the formation of adhesions which may lead to further complications after sinus or nasal surgery. The relocation of the middle turbinate toward the nasal septum may be temporary or permanent. This system may also be used prior to surgery to pull the middle turbinate away from the uncinate process to provide improved visualization of the lateral nasal cavity during surgery.

Certain embodiments may include a method of medializing a turbinate, the method comprising: coupling a flexible member to an implant; coupling the implant to an insertion device; inserting a portion of the insertion device into a nasal cavity on a first side of a septum; piercing the septum with the insertion device; directing the implant through the septum such that the implant is located on a second side of the septum; removing the insertion device from the nasal cavity; leaving the implant on the second side of the septum; and using the flexible member to secure a turbinate in a location proximal to the septum. In specific embodiments, coupling the implant to the insertion device may comprise inserting the implant in a channel in the insertion device. In particular embodiments, coupling the implant to the insertion device may comprise placing the implant against a stop in the channel. Certain embodiments may further comprise penetrating the turbinate with the insertion device. In specific embodiments piercing the septum with the insertion device may include engaging a tapered end of the insertion device with the septum. In specific embodiments, piercing the septum with the insertion device may further comprise aligning a tapered surface of the implant with the tapered end of the insertion device. In certain embodiments, the flexible member may be a suture. In particular embodiments, using the flexible member to secure the turbinate in a location proximal to the septum may comprise tying a knot in the flexible member. In certain embodiments, using the flexible member to secure the turbinate in a location proximal to the septum may comprise engaging the turbinate with a retainer secured to the flexible member. In particular embodiments, the retainer may be secured to the flexible member with a knot. In certain embodiments, the retainer may be secured to the flexible member with a projection on the flexible member.

Particular embodiments may include an implant configured for insertion into a tissue in a nasal cavity. The implant may comprise: a first end; a second end; a base portion and an upper portion, wherein the base portion is configured to be retained in a channel of an insertion device; and a tapered surface proximal to the first end. In certain embodiments, the base portion may have a cross-section that is semicircular. In particular embodiments, the base portion may be wider than the upper portion. In certain embodiments, the second end may not be configured to pierce tissue. In specific embodiments, the second end may be substantially perpendicular to an axis extending from the first end to the second end. Certain embodiments may also comprise an aperture. In certain embodiments, the aperture is in the upper portion.

Specific embodiments may comprise an insertion device configured to install an implant into a tissue in a nasal cavity. The insertion device may comprise: an elongate body having an angled portion and a handle portion; a tapered first end proximal to the angled portion; a curved portion between the angled portion and the handle portion; a channel in the angled portion; and a stop in the channel. In certain embodiments, the channel may be configured to receive the implant of claim 12. In specific embodiments, the stop may be positioned such that the tapered surface of the implant may be substantially aligned with the tapered first end of the insertion device when the implant is installed in the channel and engaged with the stop of the insertion device.

Particular embodiments may comprise an implant configured to medialize a turbinate to a septum. The implant may comprise: a main body comprising a top, a bottom, a first side, and a second side; a first barb extending from the first side; a second barb extending from the second side; and a first aperture extending through the main body, where the first aperture is proximal to the first barb. It is understood that labeling a surface the "top" or "bottom" is for reference purposes only, and is not intended to limit the implant to any specific orientation, for example, during use. In specific embodiments, the first barb may be curved downward towards the bottom of the main body as the first barb extends from the first side of the main body. In particular embodiments, the first aperture may be below first barb. Certain embodiments may further comprise a third barb and a fourth barb, each extending from the first side. Specific embodiments may further comprise a second aperture proximal to the third barb, and a third aperture proximal to the fourth barb. In particular embodiments, the first barb may be shorter than the third barb and the fourth barb.

In certain embodiments, the second barb extends perpendicular from the second side. In particular embodiments, the main body of the implant is triangular-shaped and the top of the body is locate at an intersection of the first side and the second side. In specific embodiments, the first barb is configured to penetrate mucosa of a nasal septum. In certain embodiments the second barb is configured to penetrate a turbinate.

Certain embodiments may also comprise a kit for medializing a turbinate to a septum. In specific embodiments, the kit may comprise an implant having: a main body comprising a top, a bottom, a first side, and a second side; a first barb extending from the first side; a second barb extending from the second side; and a first aperture extending through the main body, wherein the first aperture is proximal to the first barb. The kit may also comprise an insertion device comprising a handle portion, a shaft, a distal end, and a first projection proximal to the distal end. In specific embodiments, the first projection may be configured to extend through the first aperture when the implant is coupled to the insertion device. In certain embodiments, the implant may comprise a second aperture proximal to a third barb and a third aperture proximal to a fourth barb. In specific embodiments, the insertion device may comprise a second projection configured to extend through the second aperture and a third projection configured to extend through the third aperture when the implant is coupled to the insertion device. In certain embodiments, the first, second and third projections are flexible. In particular embodiments, the insertion device may comprise a recessed portion configured to engage the implant when the implant is coupled to the insertion device.

Certain embodiments comprise a method of medializing a turbinate, where the method comprises: providing an implant according to a previously-described embodiment; providing an insertion device comprising a handle portion, a shaft, a distal end, and a first projection proximal to the distal end; inserting the first projection of the insertion device through a first aperture of the implant; inserting the implant and the distal end of the insertion device into a nasal cavity between a turbinate and a septum; inserting a first barb of the implant into the septum; inserting a second barb of the implant into the turbinate; removing the first projection from the first aperture; and removing the insertion device from the nasal cavity.

In certain embodiments, removing the first projection from the first aperture may comprise rotating the insertion device about a longitudinal axis of the shaft of the insertion device. In particular embodiment, the implant may further comprise a third and fourth barb extending from the first side of the implant, and the third and fourth barb may be inserted into the septum. In certain embodiments, the implant may further comprise a second aperture proximal to the third barb and comprise a third aperture proximal to the fourth barb. In specific embodiments, the insertion device may comprise a second and third projection, and the second projection may be inserted into the second aperture, and the third projection may be inserted into the third aperture when the first projection is inserted into the first aperture. In particular embodiments, the insertion device may comprise a recessed portion proximal to the distal end. In specific embodiments, the method of claim 36 wherein the recessed portion is configured so that the second barb extends through the recessed portion when the first projection of the insertion device is inserted through the first aperture of the implant.

Certain embodiments may comprise an implant configured to secure a turbinate. The implant may comprise: an elongate body comprising a first end and a second; a tapered surface proximal to the first end; a first locking member proximal to the first end; and a second locking member proximal to the second end. In specific embodiments, the first and second locking members may each comprise a pivot. In particular embodiments, the first and second locking members may be configured to be placed in a first position that is aligned with the elongate body and a second position that is not aligned with the elongate body.

As used herein, the terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment the term "substantially" refers to ranges within 10%, preferably within 5%, more preferably within 1%, and most preferably within 0.5% of what is specified.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

The term "coupled," as used herein, is defined as connected, although not necessarily directly, and not necessarily mechanically.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of example embodiments presented here. The drawings are not to scale, and certain distances or spacings may be exaggerated to provide clarity. The drawings are examples only. They do not limit the claims.

DETAILED DESCRIPTION OF EXEMPLARY EMBODIMENTS

Figure 1:
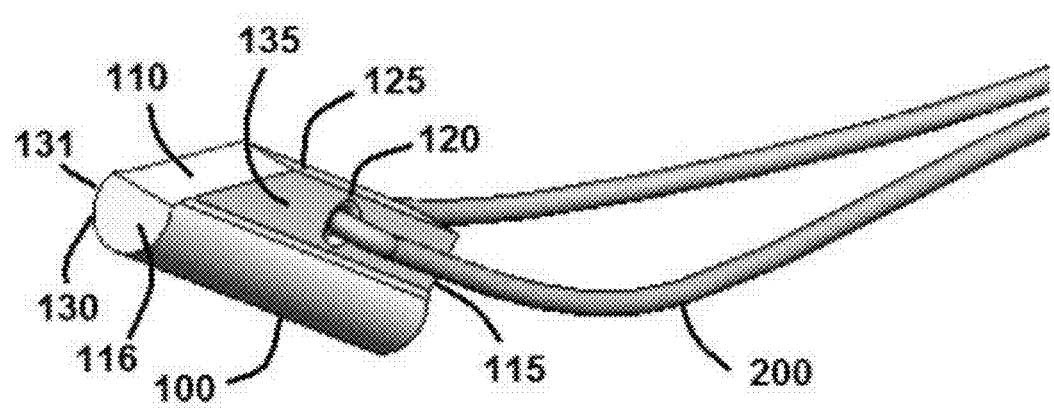
FIG. 1 is a perspective view of an implant coupled to a flexible member according to an exemplary embodiment of the present disclosure.
Figure 2:
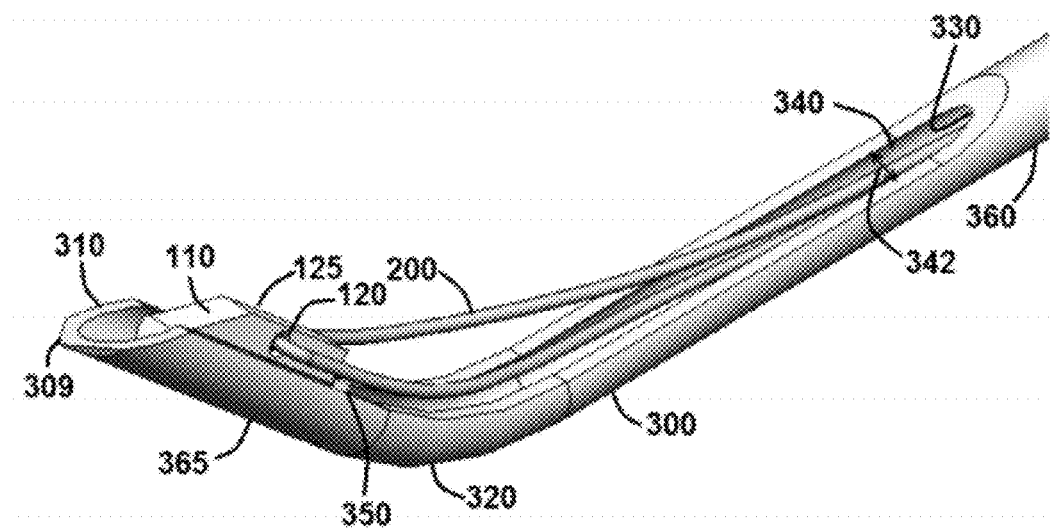
FIG. 2 is a perspective view of the implant and flexible member of FIG. 1 coupled to an insertion device.

Embodiments of the present disclosure comprise a method and system for medializing one or more turbinates in a nasal cavity. Specific embodiments comprise a method and system for displacing a middle turbinate towards a septum and holding the middle turbinate proximal to the septum. Referring initially to FIGS. 1-8, an implant 100 is coupled to a flexible member or suture 200 and an insertion device 300. In this embodiment, implant 100 comprises a tapered surface 110 proximal to a leading end 116, and a trailing end 115 that is substantially perpendicular to an axis extending between leading end 116 and trailing end 115. In the illustrated embodiment, implant 100 comprises a lateral surface 125 and an aperture 120, through which suture 200 passes. Implant 100 can be inserted into insertion device 300 so that tapered surface 110 is generally aligned with a tapered surface 310 proximal to an end 309 of insertion device 300. In the embodiment shown, insertion device 300 comprises an angled portion 365 that is angled with respect to a handle portion 360 that can be gripped by a user during installation of implant 100 with insertion device 300. Insertion device 300 may also have a curved portion 320 between angled portion 365 and handle portion 360. In the embodiment shown, insertion device 300 comprises a hollow portion 330 that allows suture 200 to pass through insertion device 300.

A portion of the external wall of insertion device 300 may be removed to reveal a groove or channel 340 formed in insertion device 300. Channel 340 can be configured to receive implant 100 prior to an installation of implant 100. In the embodiment shown, implant 100 has a cross-section with a variable width such that a base portion 130 is wider than upper portion 135. For example, base portion 130 has a semi-circular shape that is configured to fit within channel 340. As used herein, the term "base portion" includes the portion of implant 100 that is retained by channel 340. In this embodiment, base portion 130 has a shape that is more than half a circle and has a widest portion 131 that is wider than opening 342 in groove. Implant 100 can be inserted into the open end 309 of insertion device 300, but will not fall laterally out of channel 340 because widest portion 131 is wider than opening 342. Implant 100 can therefore enter and exit channel 340 via the opening at end 309 of insertion device 300. A stop 350 in channel 340 can be used to prevent implant 100 from moving farther away from end 309.

Figure 3:
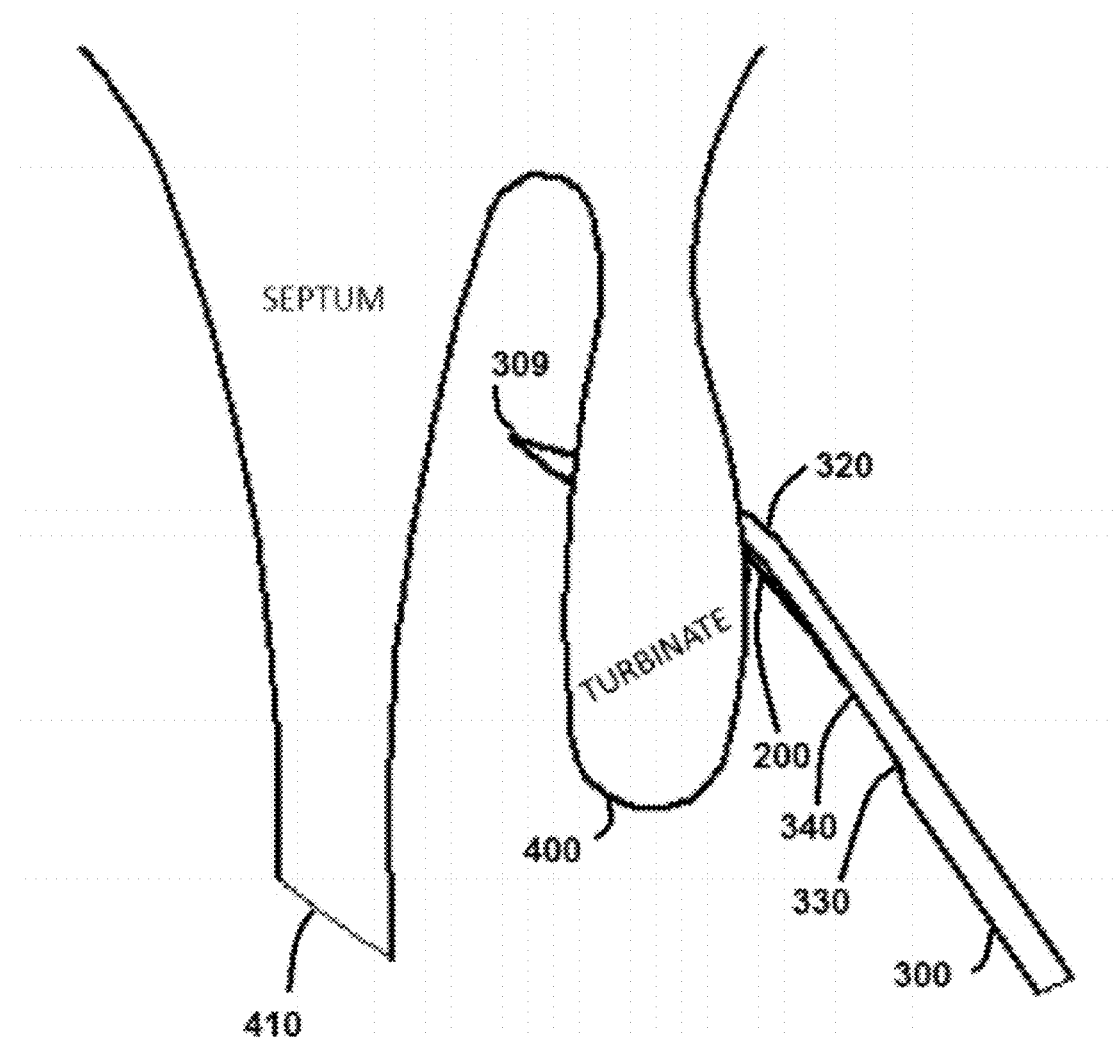
FIG. 3 is a side view of the insertion device of FIG. 2 during a method of installation.
Figure 4:
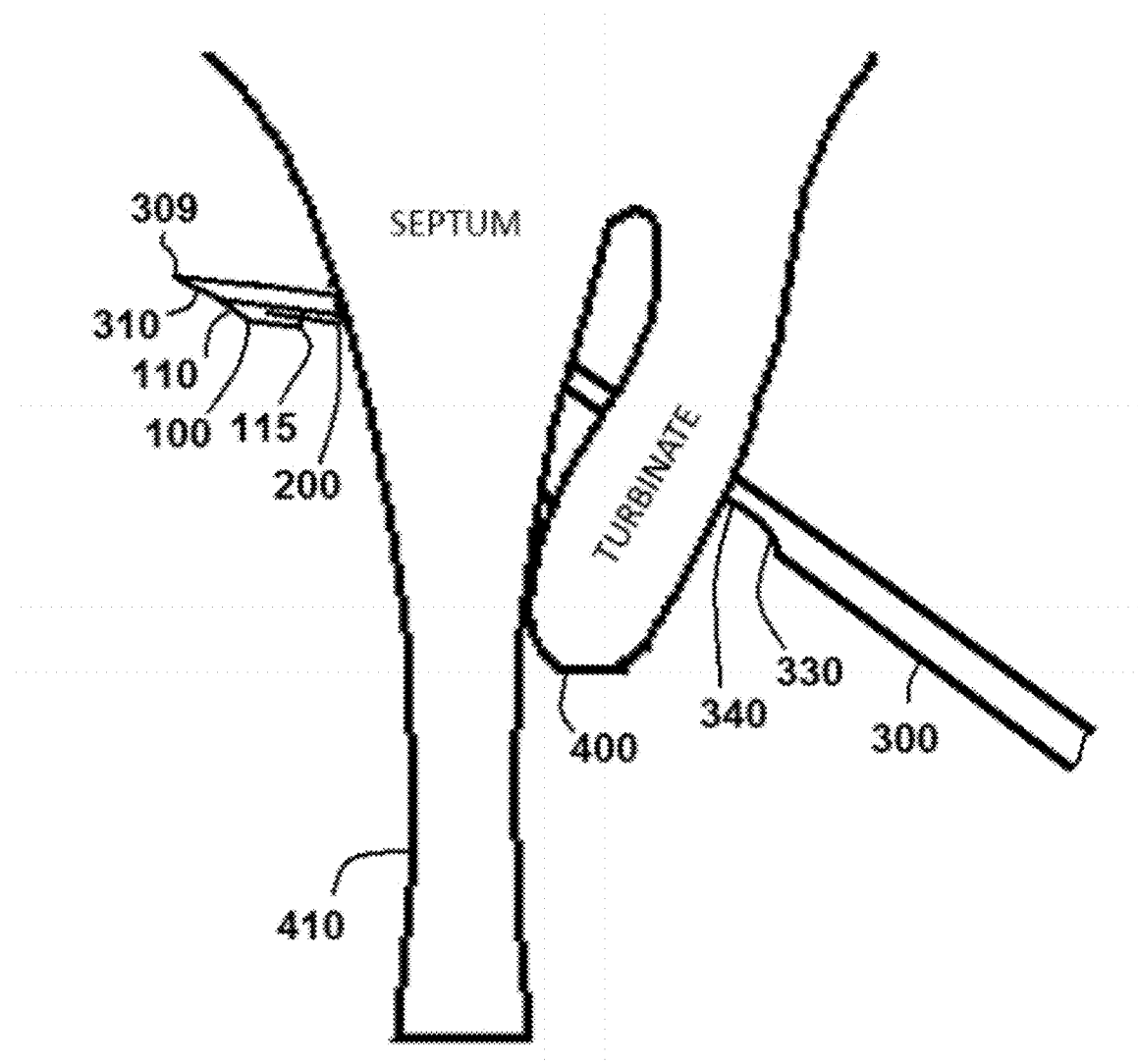
FIG. 4 is a side view of the insertion device of FIG. 2 during a method of installation.

When implant 100 is inserted into channel 340 and placed against stop 350, tapered surface 110 is generally aligned with tapered surface 310 so that they are in approximately the same plane. As shown in FIGS. 3 and 4, insertion device 300 (with implant 100 installed) can be used to penetrate a turbinate 400 (such as the middle turbinate) and a septum 410. Tapered surfaces 110 and 310 can pierce turbinate 400 and septum 410 as insertion device 300 is directed towards septum 410. As shown in FIG. 4, insertion device 300 can pierce septum 410 sufficiently for implant 100 to be placed on the side of septum 410 opposite of turbinate 400. When implant 100 is so positioned, insertion device 300 can be withdrawn. As shown in FIGS. 2-5, the portion of insertion device 300 that penetrates turbinate 400 and septum 410 (e.g., the portion comprising channel 340) has a smaller cross-section than the remainder of insertion device 300. This configuration allows insertion device 340 to more easily penetrate turbinate 400 and septum 410 and minimizes the trauma cause to turbinate 400 and septum 410.

Trailing end 115 of implant 100 (e.g., the end of implant 100 that is opposite of leading end 116 and tapered surface 110) is configured so that it will not pass through septum 410 (or another tissue through which it has been inserted) when insertion device 300 is retracted. As insertion device 300 is withdrawn or refracted from the position shown in FIG. 4, trailing end 115 will engage septum 410. As insertion device 300 is further retracted, trailing end 115 will stay engaged with septum 410 and implant 100 will slide within channel 340 towards end 309. When insertion device 300 is withdrawn enough so that end 309 passes back through septum 410, implant 100 will not pass through septum 410 (e.g., trailing edge 115 is not configured to penetrate septum 410, and implant 100 is allowed to freely slide towards end 309 when trailing edge 115 engages septum 410).

Figure 5:
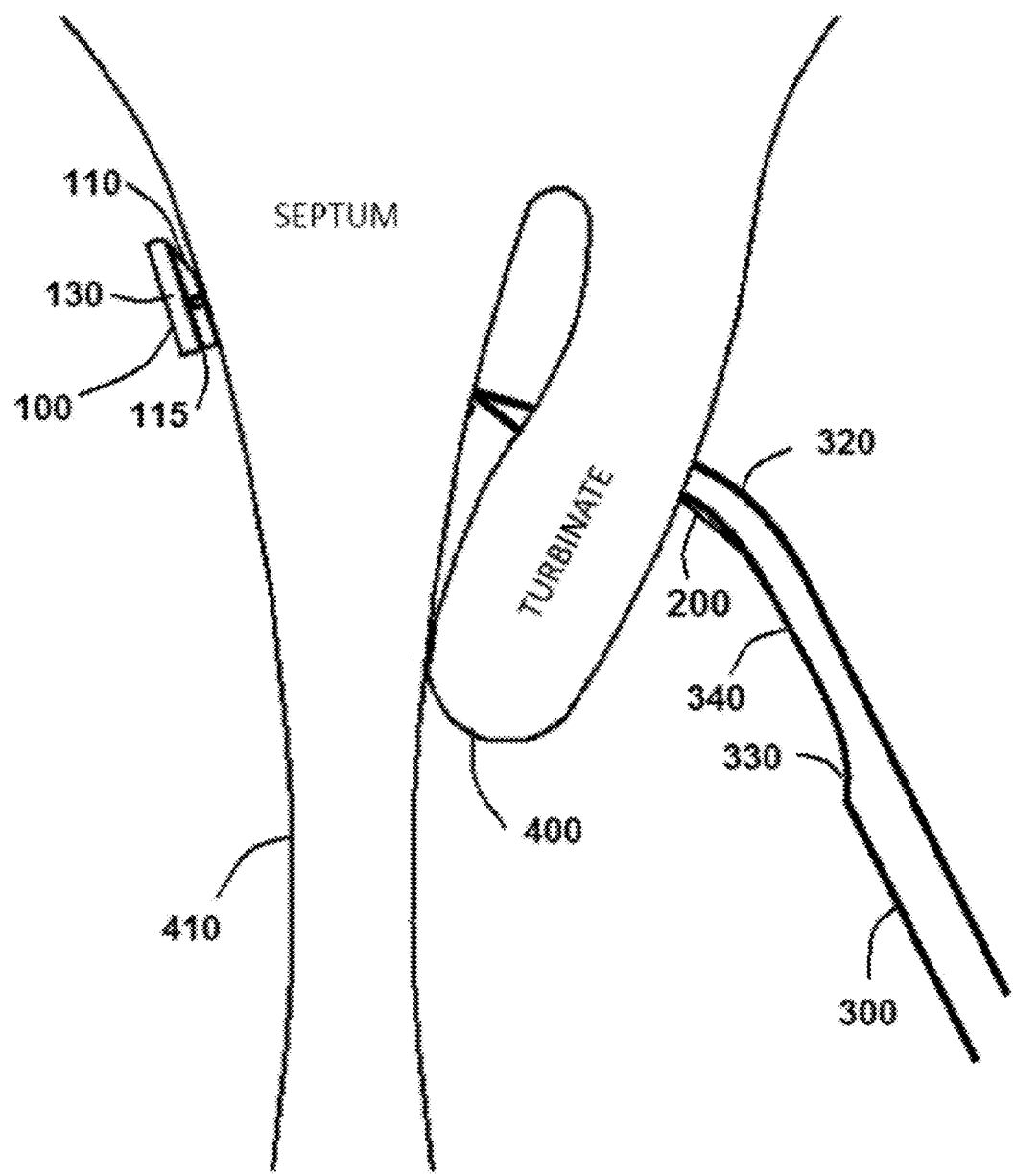
FIG. 5 is a side view of the insertion device of FIG. 2 during a method of installation.
Figure 6:
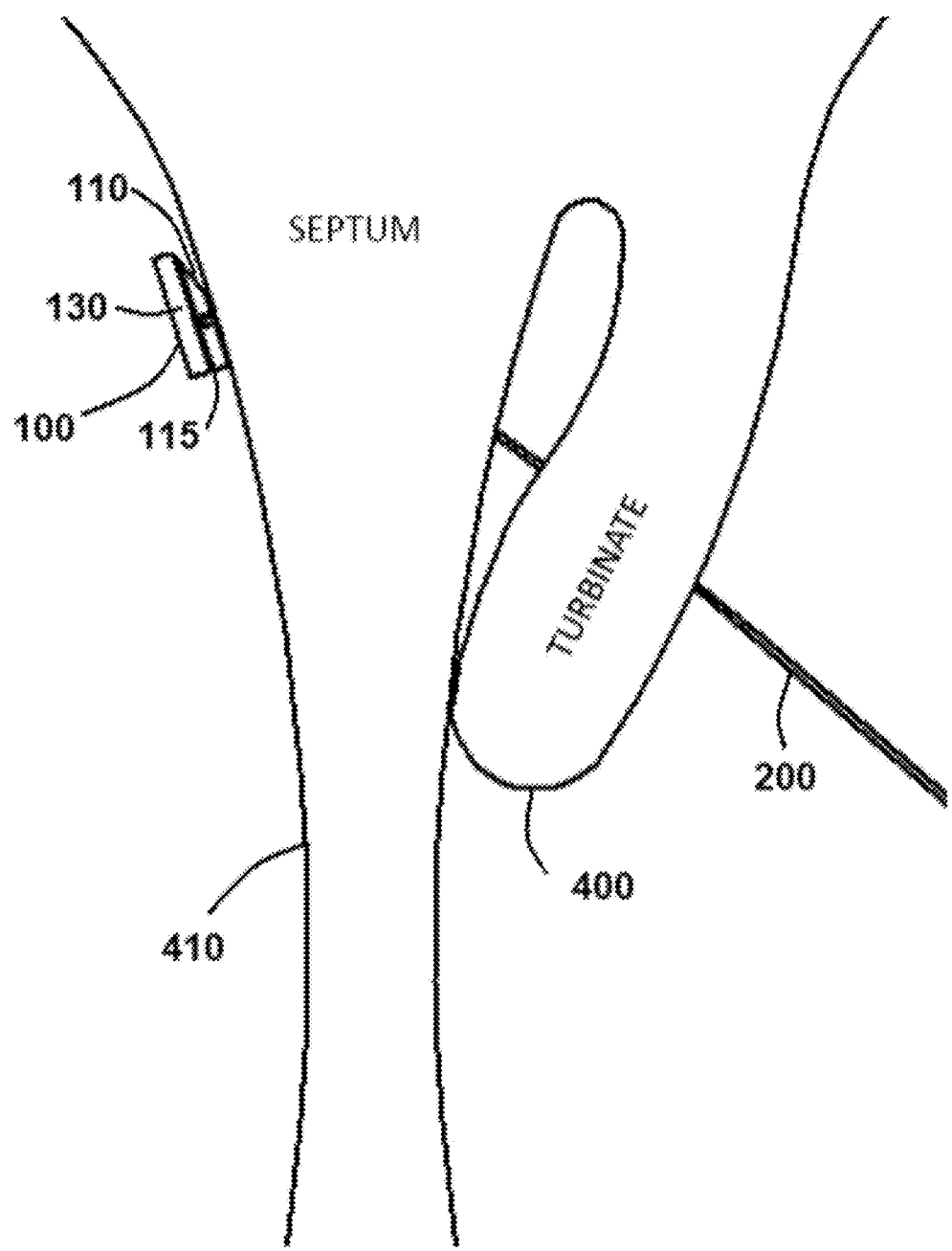
FIG. 6 is a side view of the implant and flexible member of FIG. 1 during a method of installation.
Figure 7:
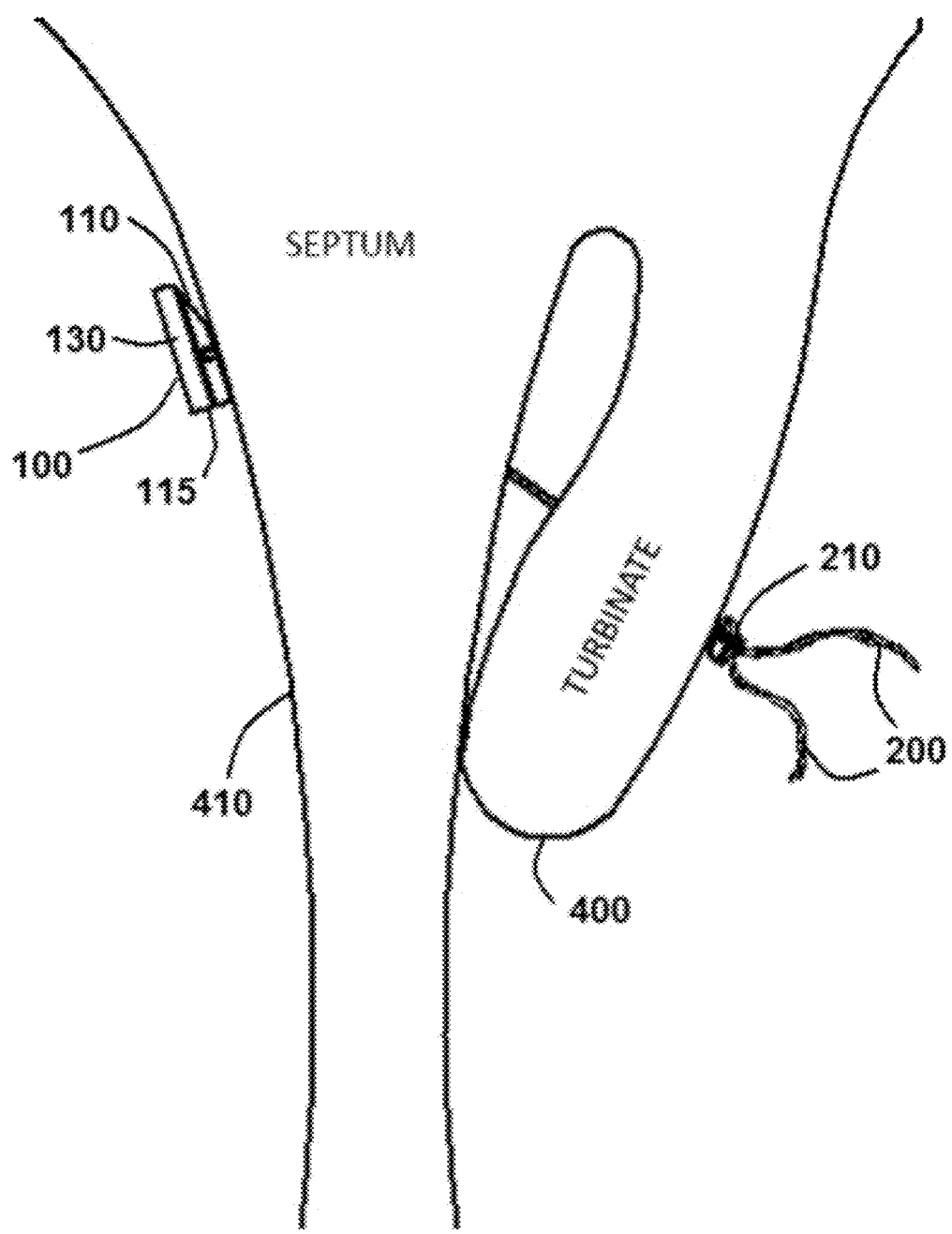
FIG. 7 is a side view of the implant and flexible member of FIG. 1 during a method of installation.
Figure 8:
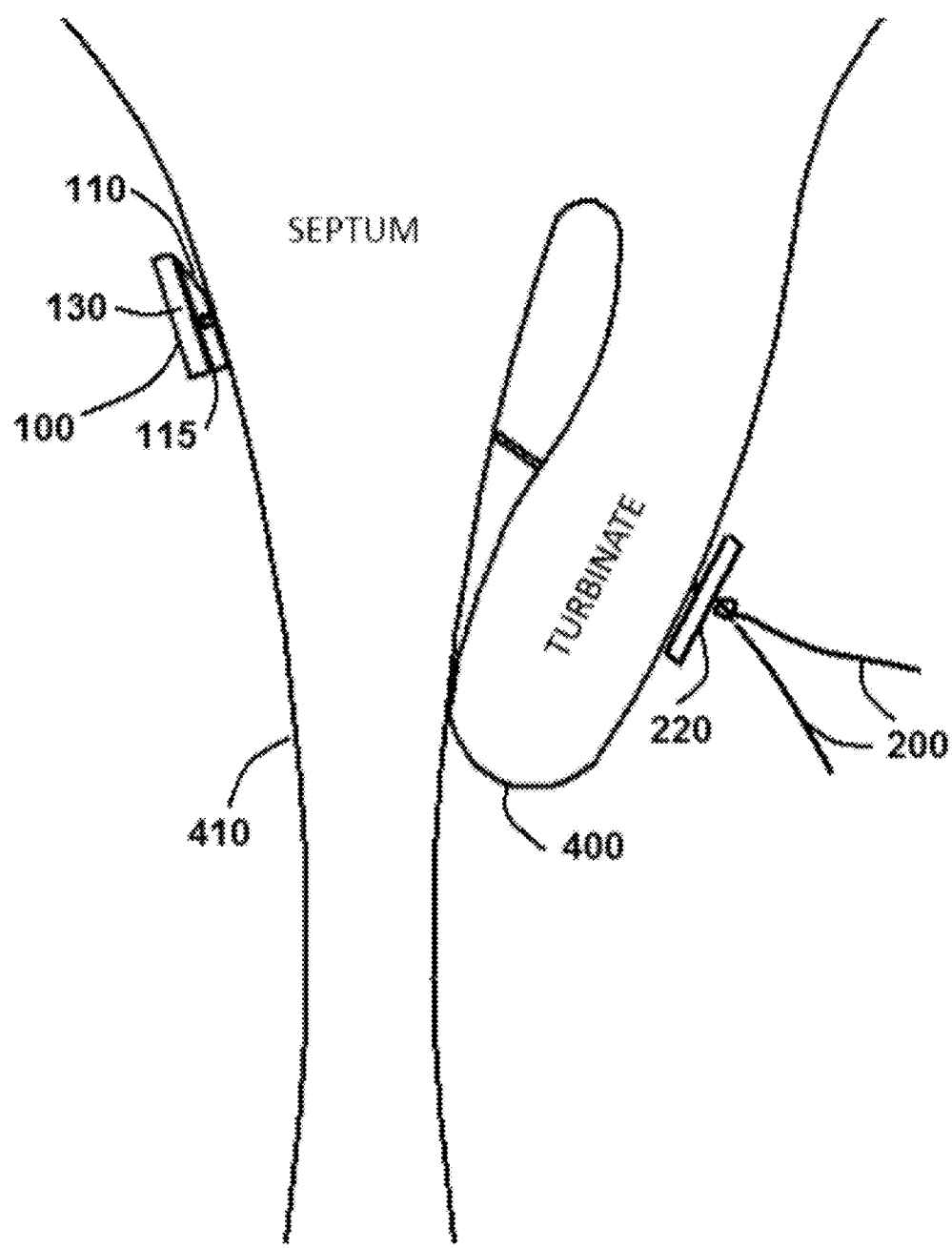
FIG. 8 is a side view of the implant and flexible member of FIG. 1 and a retainer during a method of installation

As shown in FIG. 5, implant 100 will remain on one side of septum 410 while end 309 is withdrawn to the opposite side of septum 410. Suture 200 will remain coupled to implant 100 and insertion device 300. Suture 200 can pass through an aperture (not visible in the figures) created in turbinate 400 and septum 410 by insertion device 300. As tension is placed on suture 200, implant 100 will rotate so that aperture 120 is proximal to septum 410. In the embodiment shown, lateral surface 125 is placed against septum 410. Lateral surface 125 is configured so that it is larger than the aperture created in septum 410 by insertion device 300. With implant 100 in the position shown in FIG. 5, implant 100 is even less likely to pass back through septum 410 while insertion device 300 is being removed. As shown in FIG. 6, insertion device 300 can be removed so that suture 200 is withdrawn from channel 340 and hollow portion 330 of insertion device 300. Turbinate 400 can be directed towards septum 410 and a knot 210 can be tied in suture 200 to secure turbinate 400 in a position so that it is proximal to septum 410, as shown in FIG. 7. In certain embodiments, knot 210 may be tied in suture 200 prior to the placement of implant 100 and configured to slide into the position shown in FIG. 7 prior to securing knot 210 into place. As shown in FIG. 8A, in still other embodiments, a retainer 220 may be used to retain turbinate in the desired position. Retainer 220 may be secured via a knot similar to knot 210, or in any other manner known to those skilled in the art.

Figure 9A:
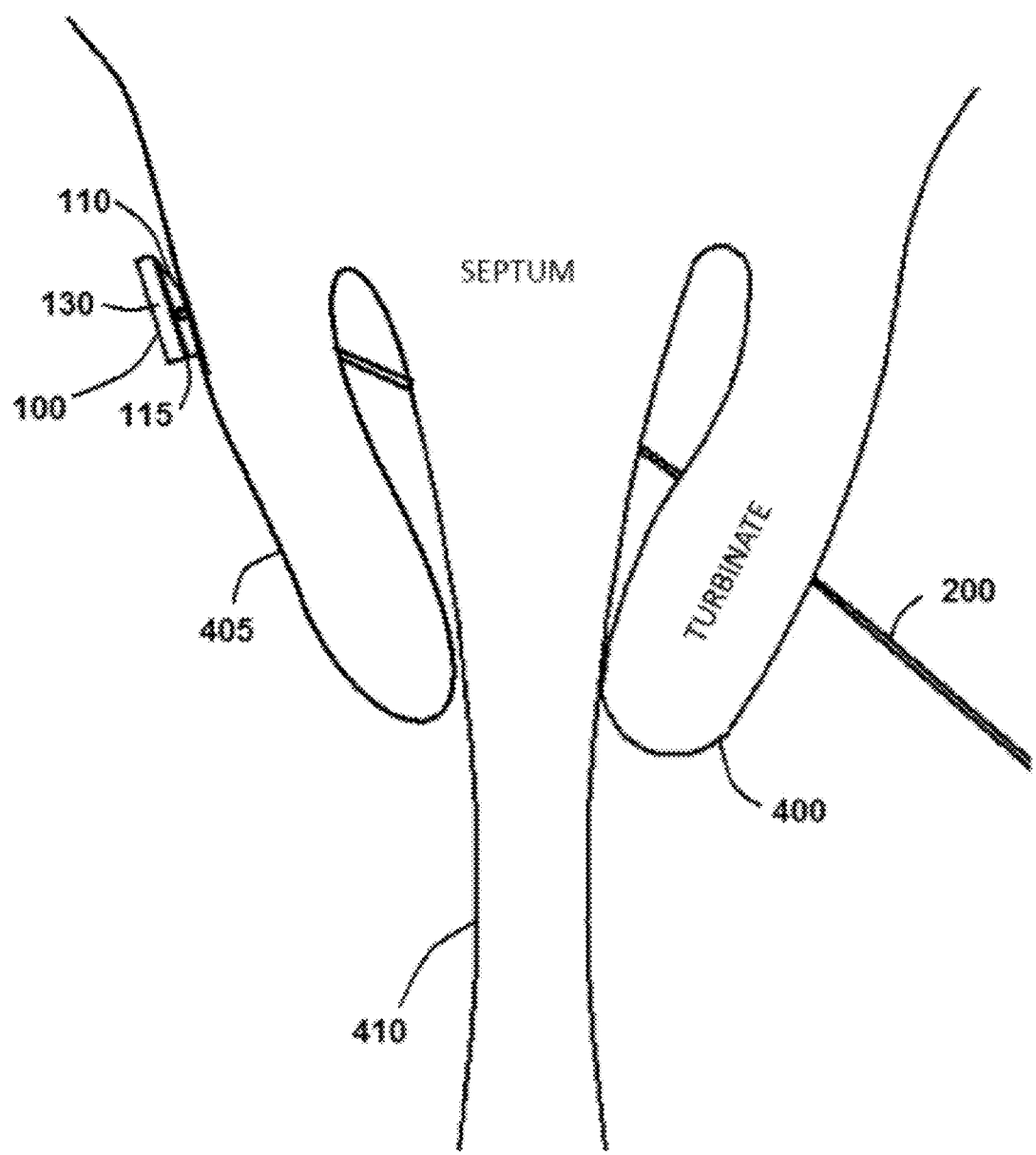
FIG. 9A is a side view of the implant and flexible member of FIG. 1 during a method of installation.

Referring now to FIG. 9A, in certain embodiments, implant 100 may be installed in a manner to capture a turbinate 405 on the side opposite of septum 410 from turbinate 400. Insertion device 300 may be used to pierce turbinate 400, septum 410, and turbinate 405 in order to place implant in the position shown in FIG. 9A. The other steps in the process to secure turbinate 405 are equivalent to those described above for turbinate 400. For example, a knot or retainer may be used to secure turbinate 400 in the position shown in FIG. 9A. The tension on suture 200 between implant 100 and the knot or retainer will also cause turbinate 405 to be deflected towards septum 410.

As shown in FIGS. 9B-9E, more than one implant 100 may be used to secure one (or more) turbinates. In the embodiment shown in FIG. 9B, a pair of implants 100 are inserted through septum 410. A suture 200 is coupled to each implant, and a knot 210 is tied in suture 200 on the opposite side of turbinate 400 from septum 410. Knot 210 may be a sliding knot that allows it to be positioned so that turbinate 400 is held in the desired location. Suture 200 may be coupled to implants 100 before implants 100 are inserted through septum 410, or may be coupled to implants 100 after they are installed in the desired location. In certain embodiments, suture 200 may not comprise knot 210, but may instead be a fixed length that is used to secure turbinate 400. Suture 200 may extend through turbinate 400 or may extend around turbinate 400. Suture 200 may also comprise a unitary piece of material that is coupled to each implant 100, or may comprise separate pieces of material coupled to each implant 100.

Figure 9B:
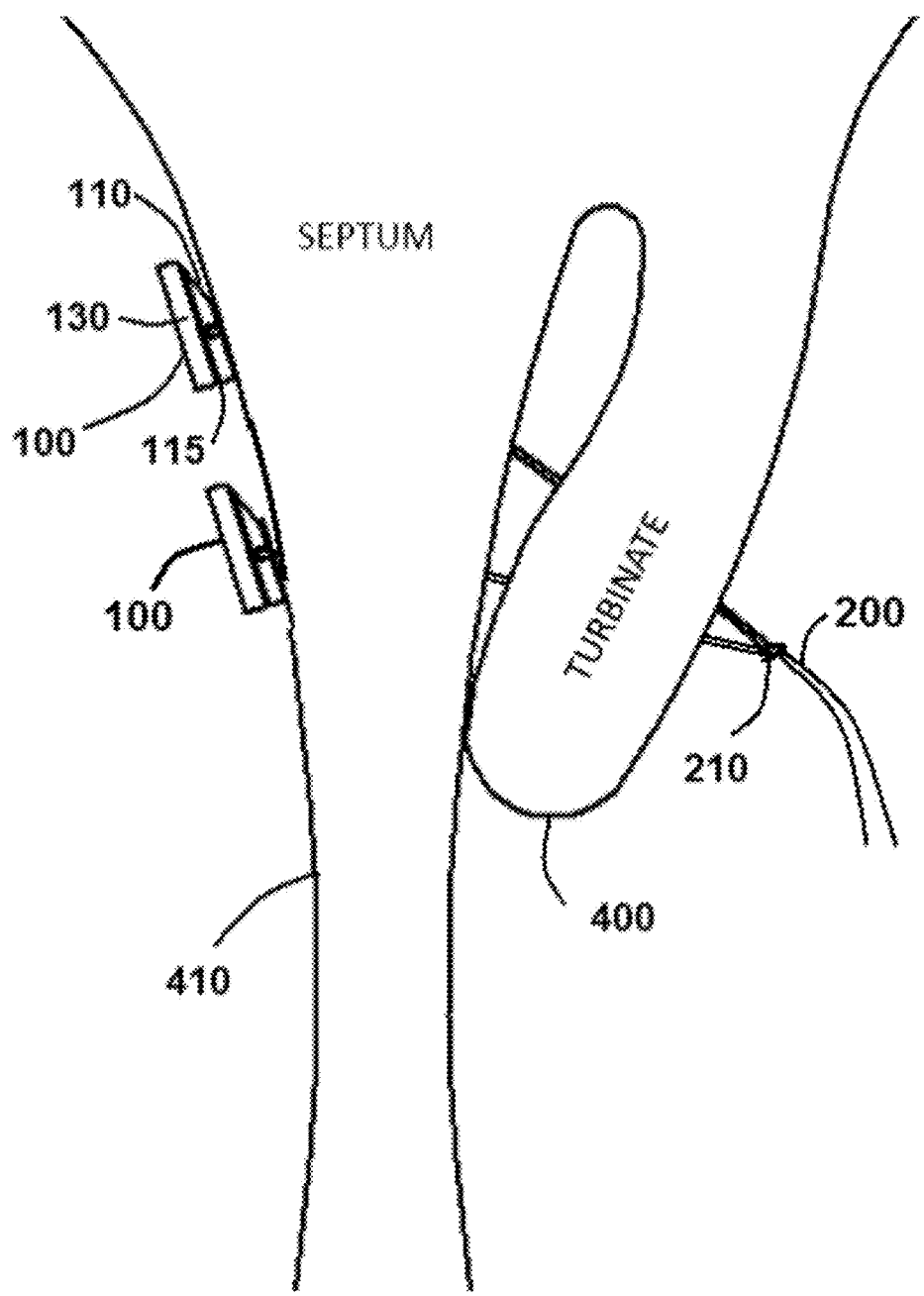
FIG. 9B is a side view of first turbinate medializing system during a method of installation according to an exemplary embodiment of the present disclosure.
Figure 9C:
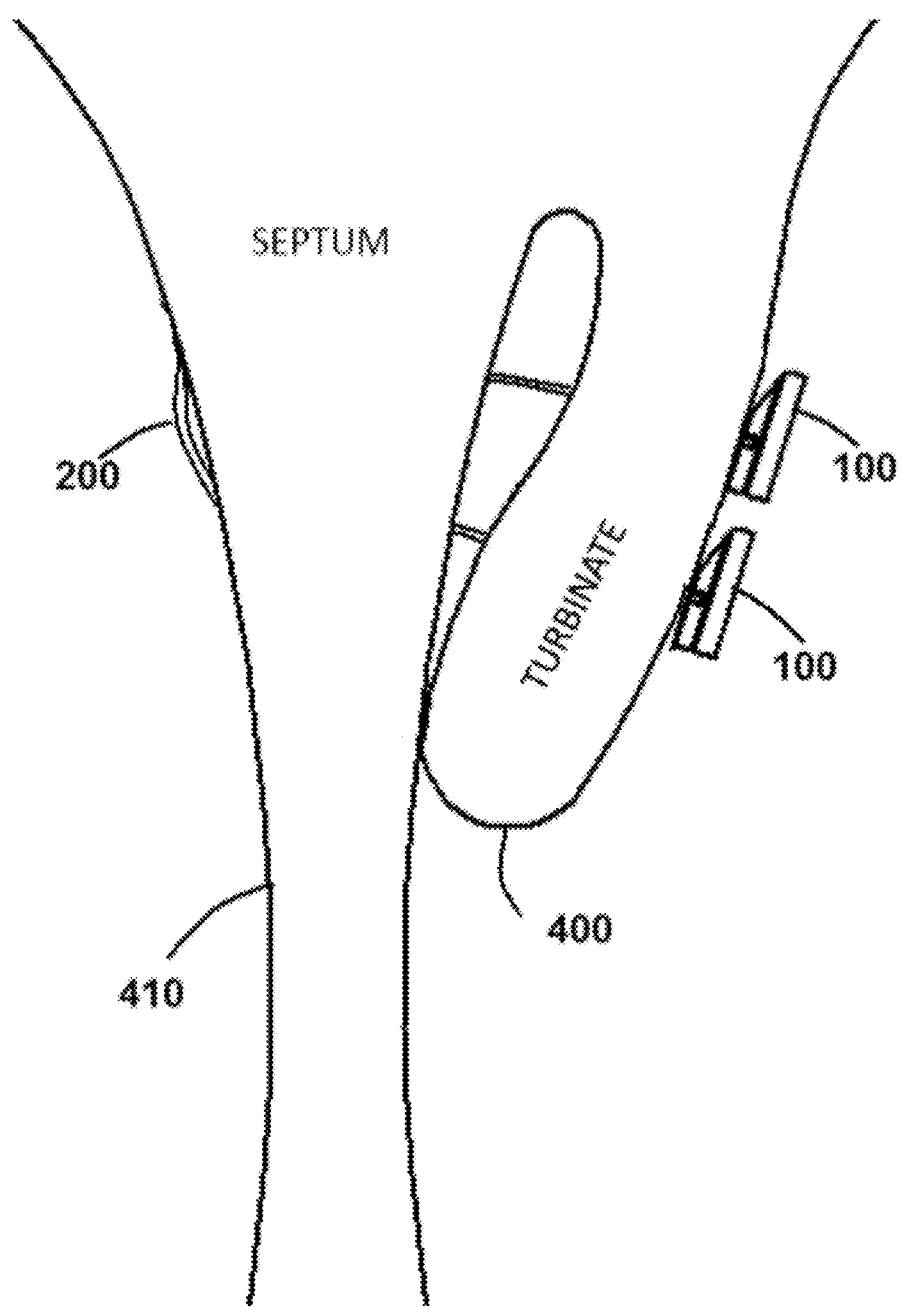
FIG. 9C is a side view of second turbinate medializing system during a method of installation according to an exemplary embodiment of the present disclosure.

Referring now to FIG. 9C, an embodiment is shown that is similar to that depicted in FIG. 9B. However, in this embodiment, implants 100 are positioned proximal to turbinate 400 rather than septum 410. In the embodiment shown, suture 200 is a unitary piece that is coupled to implants 100. It is understood that other embodiments may comprise a knot similar to knot 210 shown in FIG. 9B.

Figure 9D:
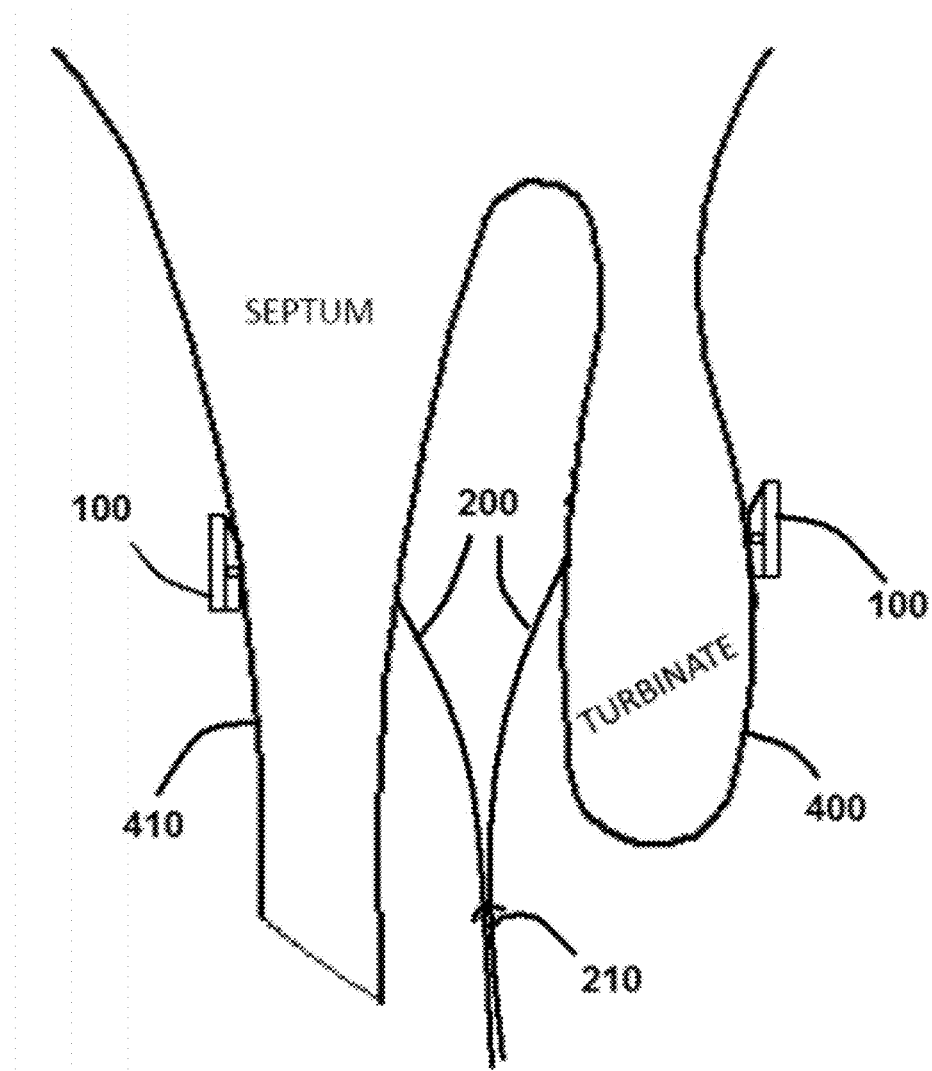
FIG. 9D is a side view of third turbinate medializing system during a method of installation according to an exemplary embodiment of the present disclosure.

As shown in FIG. 9D, one implant 100 may be installed through septum 410, while a second implant 100 may be installed through turbinate 400. Suture 200 is coupled to each implant 100, and a knot 210 (or other locking device) can be used to couple the portions of suture 200 that extend to each implant 100. In certain embodiments, knot 210 may be a sliding knot that allows knot 210 to be moved to different locations to secure turbinate 400 in the desired position.

Figure 9E:
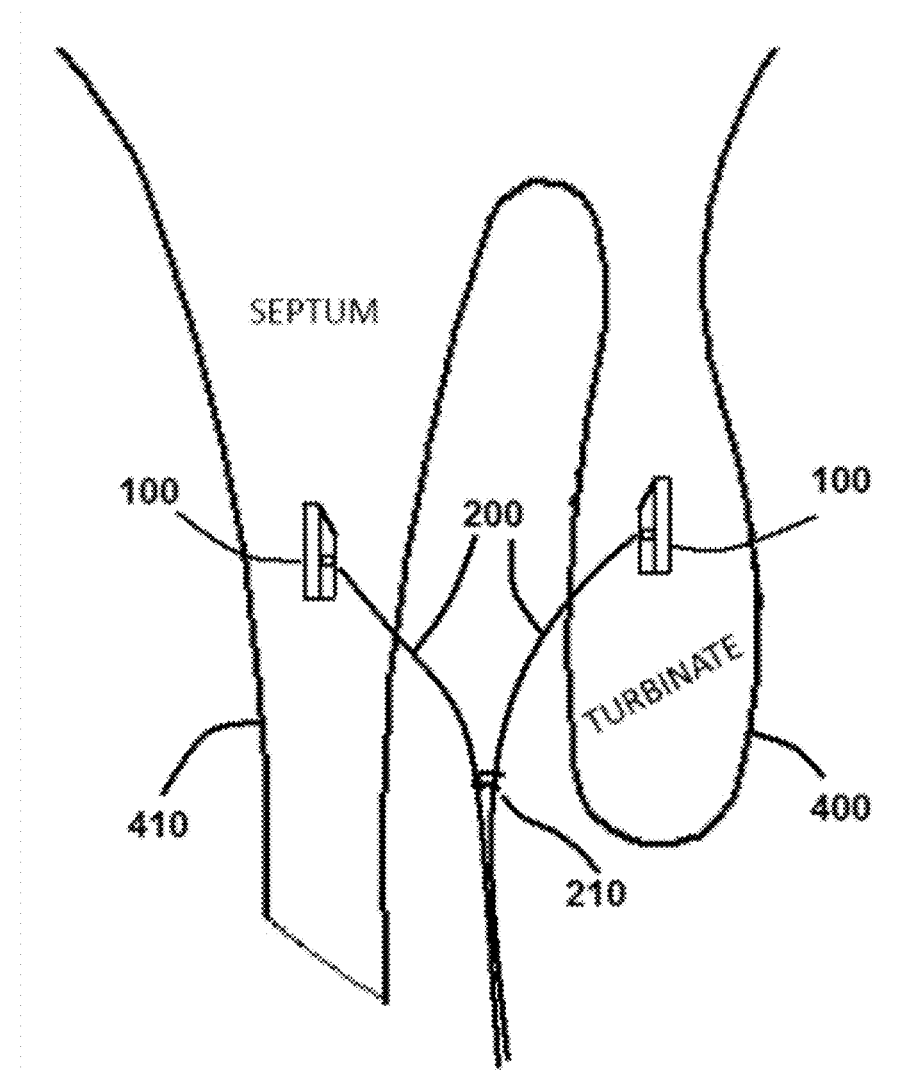
FIG. 9E is a side view of fourth turbinate medializing system during a method of installation according to an exemplary embodiment of the present disclosure.

Referring now to FIG. 9E, another embodiment is similar to that shown in FIG. 9D. In this embodiment, however, implants 100 are installed in turbinate 400 and septum 410, rather than pushed through turbinate 400 and septum 410. It is understood that any of the embodiments disclosed herein may be modified so that the implant is installed in turbinate 400 and/or septum 410.

Figure 9F:
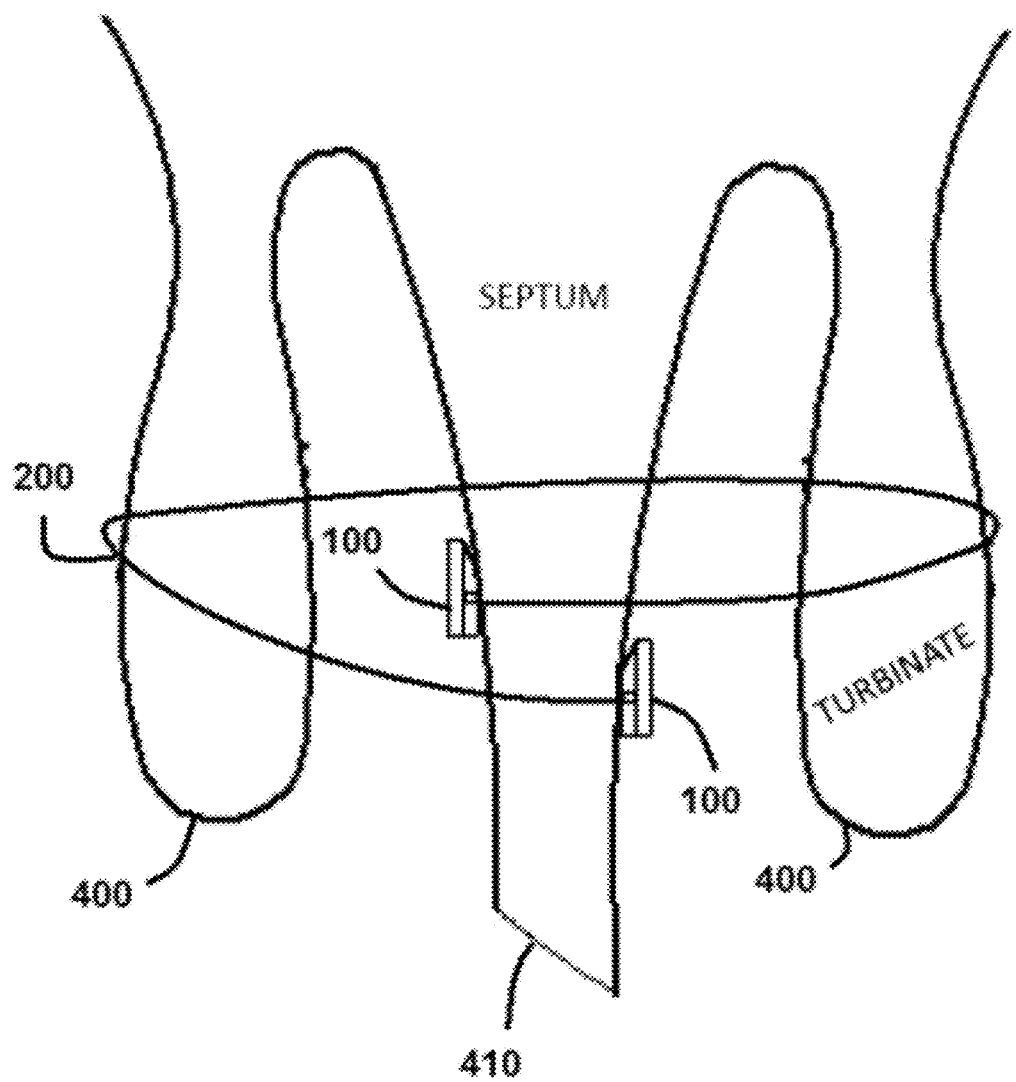
FIG. 9F is a side view of fifth turbinate medializing system during a method of installation according to an exemplary embodiment of the present disclosure.

Referring now to FIG. 9F, another embodiment comprises a pair of implants 100 inserted through opposing sides of septum 410. A first implant 100 is installed through septum 410 from the left side of septum 410 to the right side of septum 410 (as shown in FIG. 9F). In addition, a second implant 100 is installed from the right side of septum 410 to the left side of septum 410. Implants 100 are coupled via a suture 200 that extends around (or through) turbinates 400 such that turbinates 400 are secured proximal to septum 410.

Figure 9G:
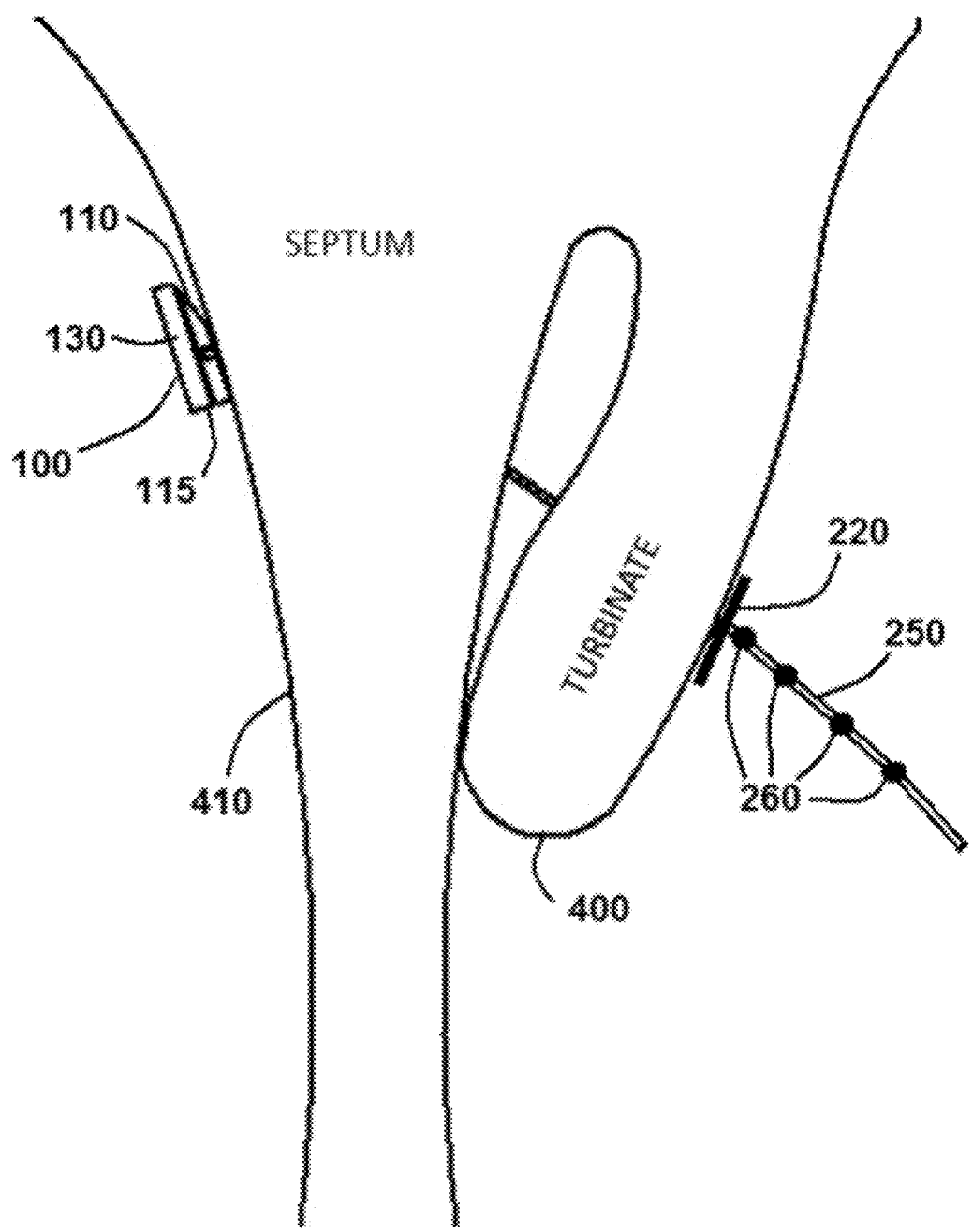
FIG. 9G is a side view of sixth turbinate medializing system during a method of installation according to an exemplary embodiment of the present disclosure.

As shown in FIG. 9G, another embodiment may comprise an implant 100 coupled to a flexible member 250. In this embodiment, implant 100 and a portion of flexible member 250 are inserted through turbinate 400 and septum 410. Flexible member 250 comprises a series of projections 260 configured to hold retainer 220 in a desired position. Retainer 220 is configured so that it can be forced past a projection 260 and toward implant 100 during the installation process. Retainer 220 is also configured so that it will not move past a projection 260 in the direction away from implant 100 after it is installed in the desired location. Projections 260 are spaced along flexible member 250 so that retainer 220 can be placed in any number of positions to position turbinate 400 proximal to septum 410.

Figure 10A:
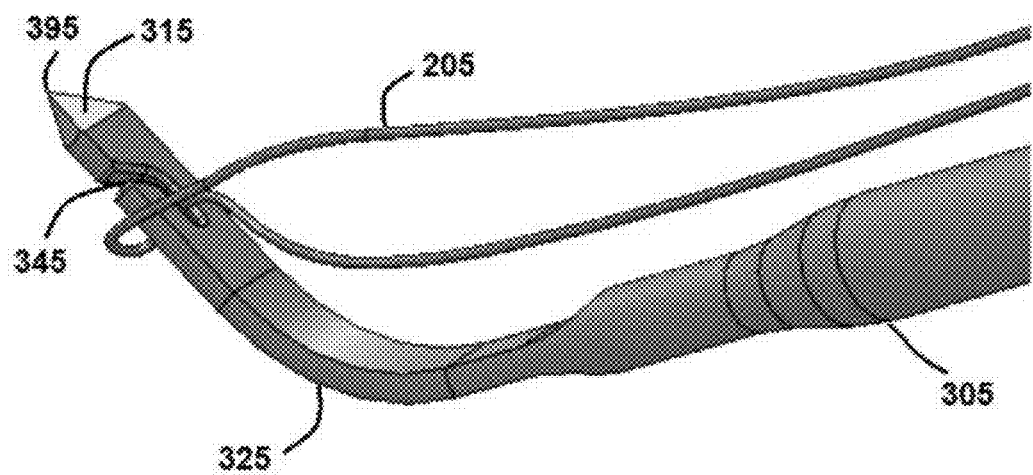
FIG. 10A is a perspective view of an insertion device and flexible member according to an exemplary embodiment of the present disclosure.

In still other embodiments, an implant may not be used to secure a turbinate proximal to the septum. Instead, a flexible member or suture may be inserted through the turbinate and septum and a knot can be tied in the suture. Referring now to FIG. 10A, an insertion device 305 comprises a curved portion 325 and a pointed or tapered surface 315 proximal to an end 395. Insertion device 305 further comprises a retaining channel or slot 345 configured to retain a suture 205. Insertion device 305 can be used to pierce a turbinate and septum (not shown) in a manner similar to that described above in the discussion of insertion device 300. However, rather than inserting an implant through the turbinate and septum, insertion device 305 inserts suture 205 through the turbinate and septum. Retaining slot 345 can be configured so that suture 205 is retained as insertion device 305 is pushed through tissue such as the turbinate or septum. Retaining slot 345 can also be configured so that as insertion device 305 is withdrawn back through tissue, suture 205 will become disengaged from retaining slot 345.

Figure 10B:
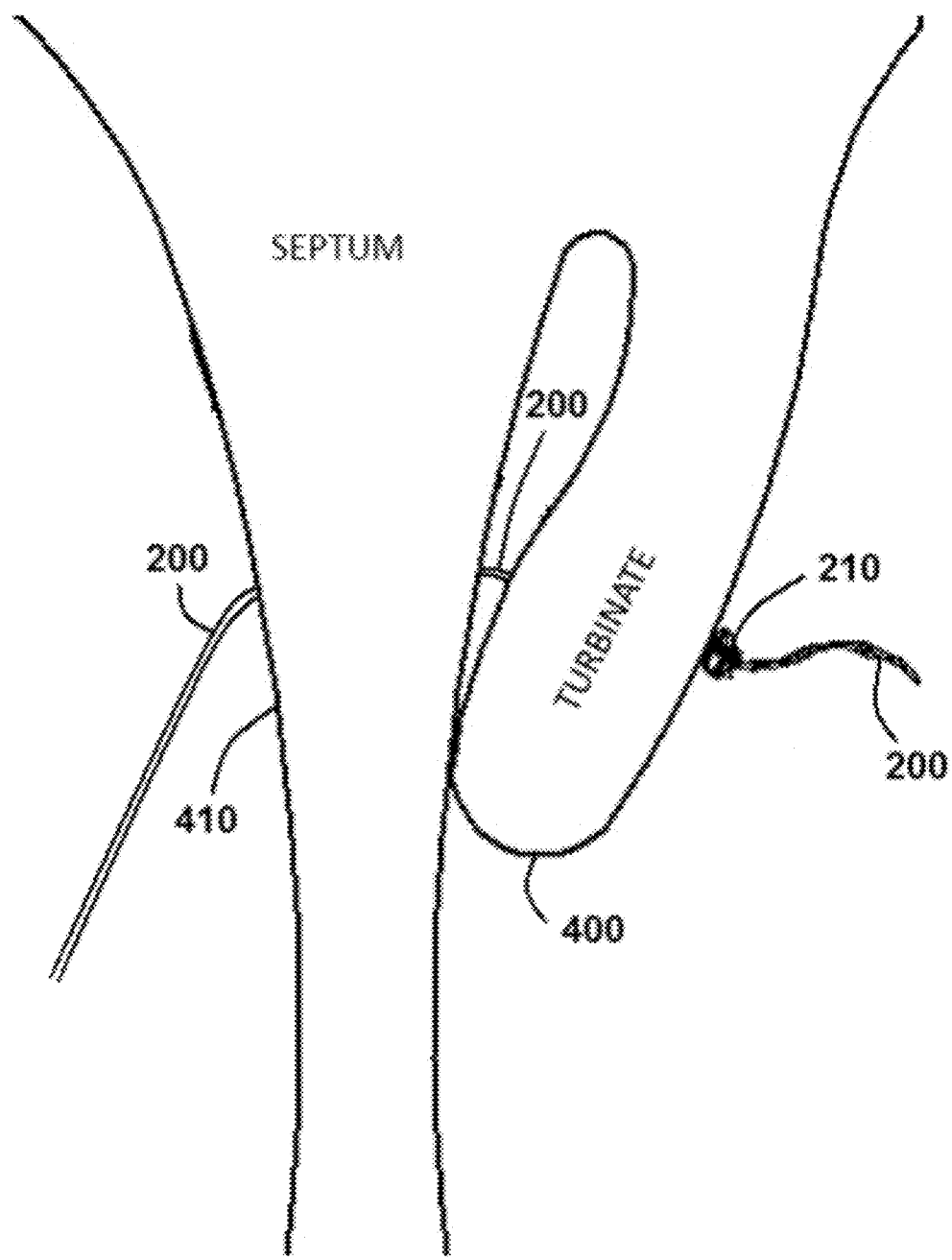
FIG. 10B is a side view of a flexible member during a method of installation according to an exemplary embodiment of the present disclosure.
Figure 10C:
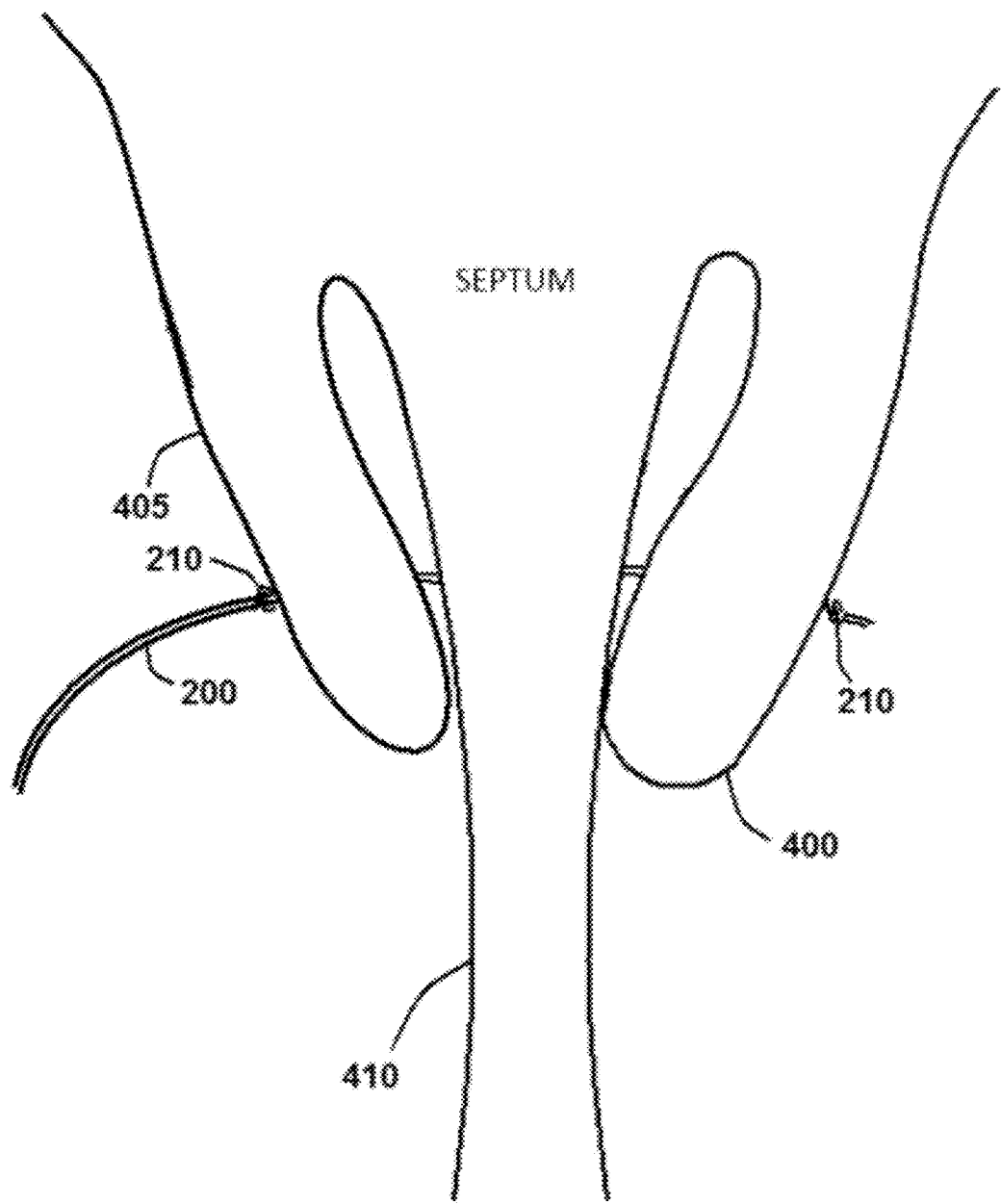
FIG. 10C is a side view of a flexible member during a method of installation according to an exemplary embodiment of the present disclosure.

One or more knots (not shown) can be tied in suture 205 to secure the turbinate proximal to the septum. In certain embodiments, more than one knot can be tied in suture 205 after it has been inserted through the turbinate and septum. For example, as shown in FIG. 10B knot 210 can be tied in the portion of suture 205 that is on the side of turbinate 400 opposite of septum 410. Another knot or securement device (not shown) can be located in the portion of suture 205 that is on the side of the septum 410 that is opposite of turbinate 400. Therefore, suture 205 can be used to secure the turbinate proximal to the septum. In certain embodiments, a knot can be tied in a portion of suture 205 prior to the insertion of suture 205 through the turbinate and/or septum. For example, a knot can be tied in a portion of suture 205 that is distal from retaining slot 345 prior to insertion of suture 205. After insertion device 305 has been used to insert suture 205 through the turbinate and septum, another knot can be tied in suture 205 (or a retainer similar to retainer 220) can be used to secure turbinate 400 to septum 410. In the embodiment shown in FIG. 10C, suture 200 has been passed through both turbinates 400 and septum 410. A knot 210 (or other retaining device) can be located on suture 200 as shown in order to secure turbinates 400 proximal to septum 410.

In another embodiment, an implant can be installed between the mucosa and septum of a patient. Referring now to FIGS. 11-23A an insertion device 550 may be used to install an implant 500 between a turbinate 400 and a septum 410 (shown in FIG. 23). In this embodiment, implant 500 comprises a main body 505, a turbinate projection or barb 510, three septum projections or barbs 515, and three apertures 520. Apertures 520 are located just below the portion where barbs 515 are coupled to main body 505, and apertures 520 extend through main body 505. It is understood that in other embodiments, the number and location of the barbs and apertures may be varied from the embodiment shown.

Figure 11:
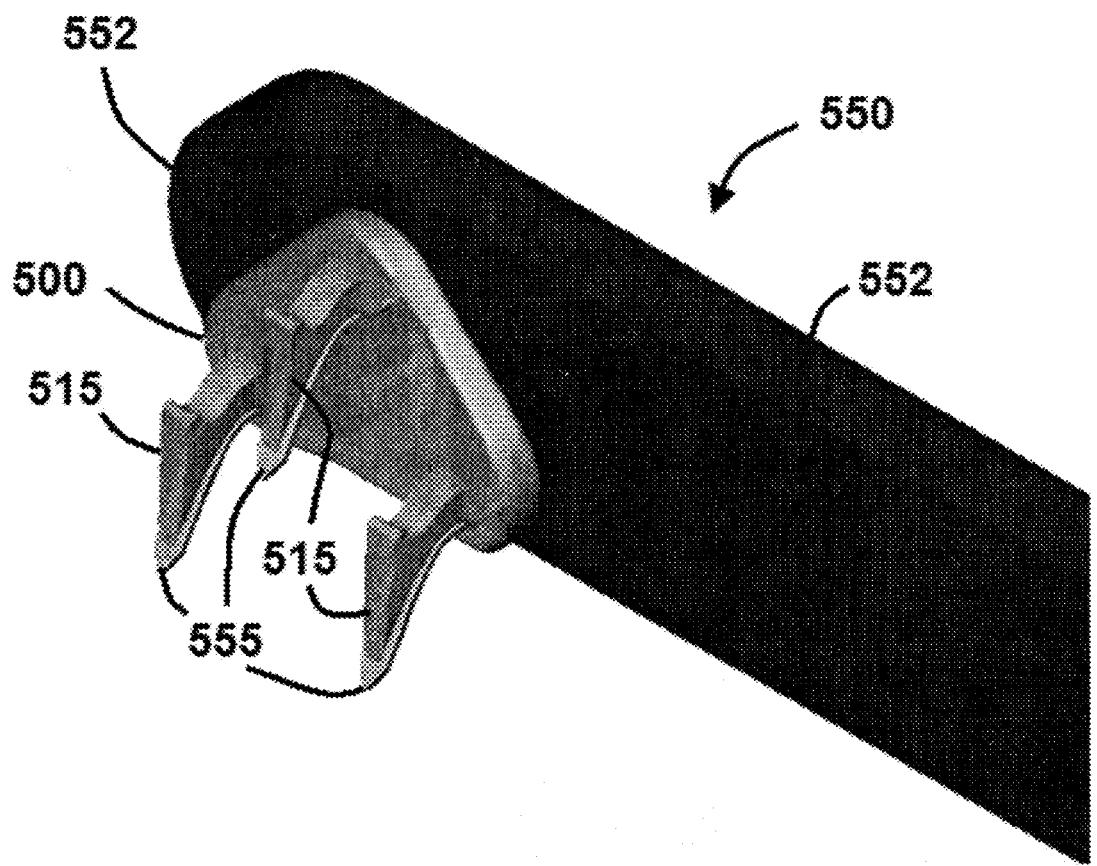
FIG. 11 is a perspective view of an implant and an insertion device according to an exemplary embodiment of the present disclosure.
Figure 12:
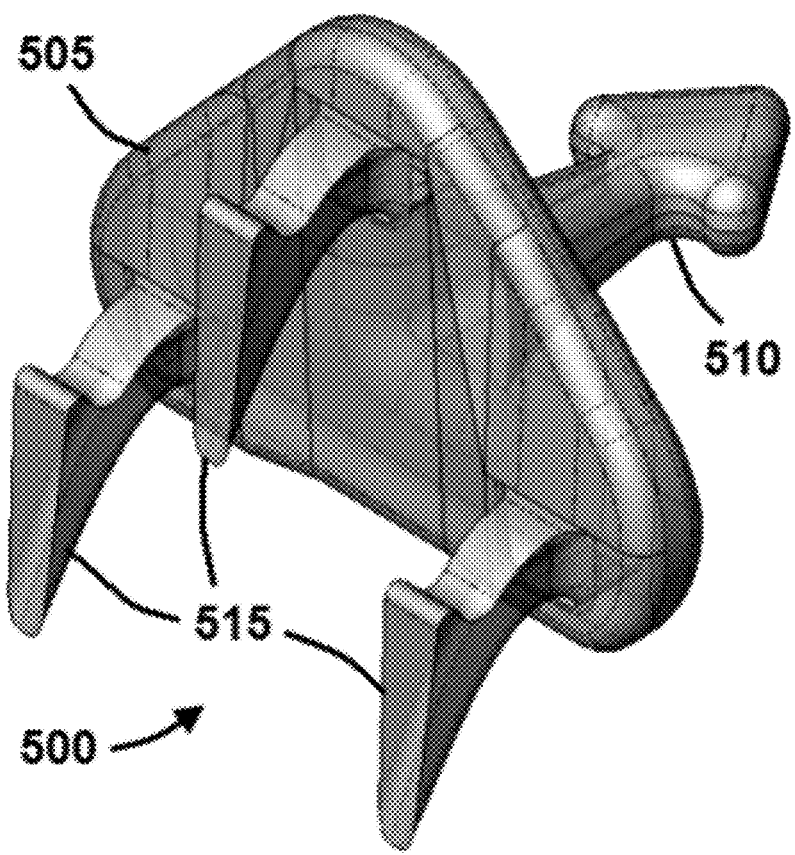
FIG. 12 is a perspective view of the implant of FIG. 11.
Figure 13:
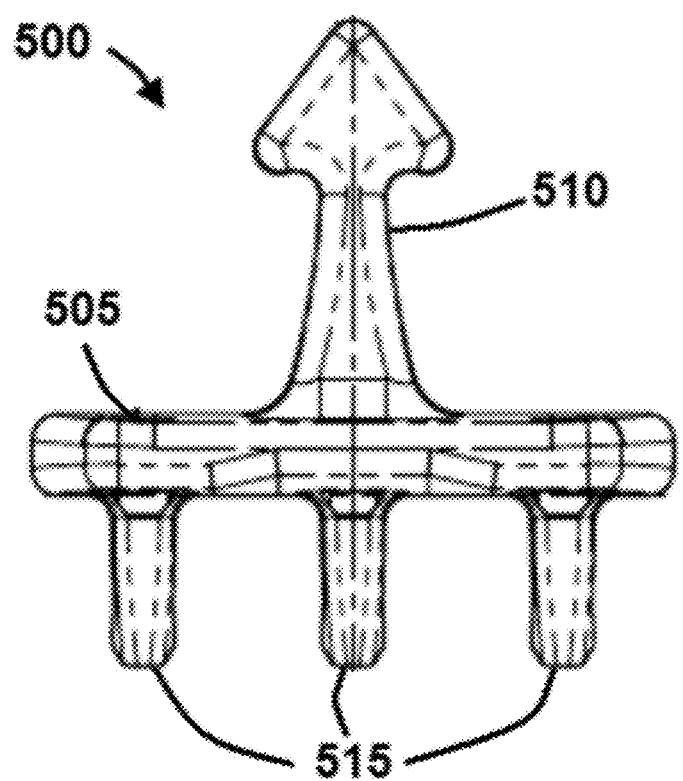
FIG. 13 is a top view of the implant of FIG. 11.
Figure 14:
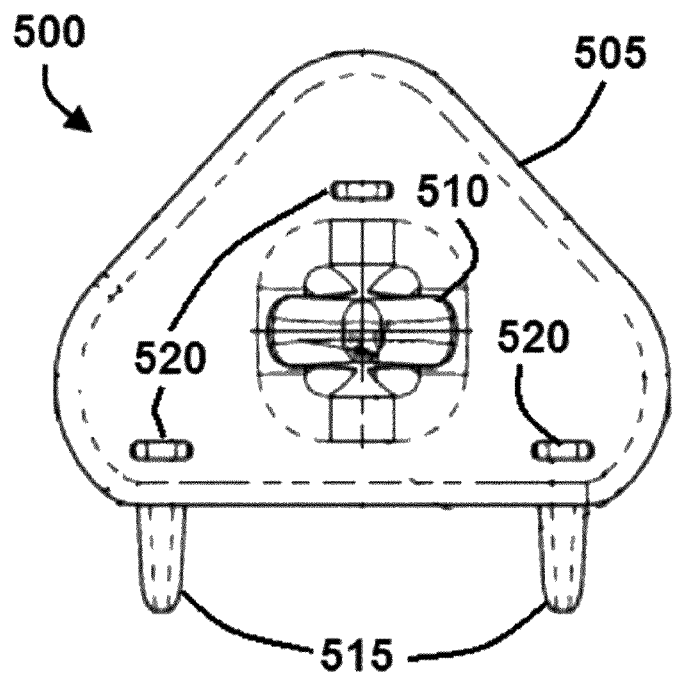
FIG. 14 is a back view of the implant of FIG. 11.
Figure 15:
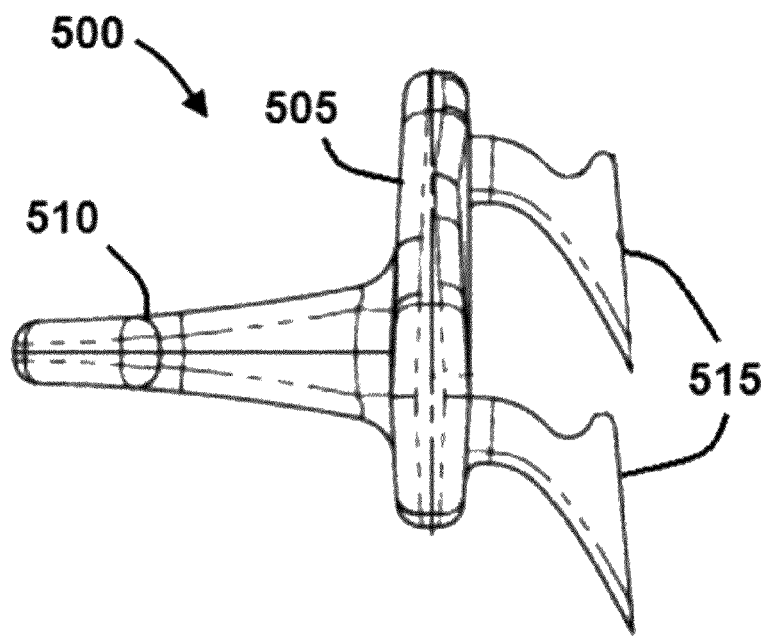
FIG. 15 is a side view of the implant of FIG. 11.
Figure 16:
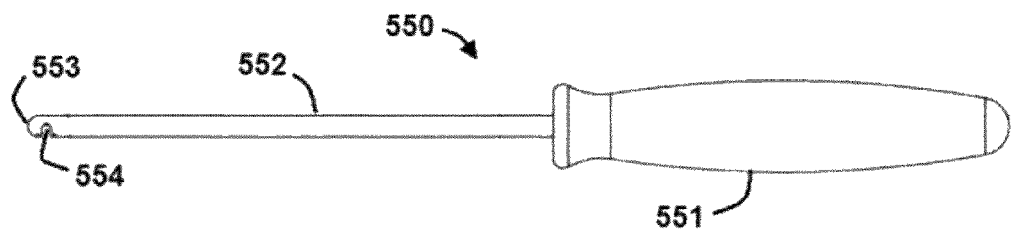
FIG. 16 is a front view of the insertion device of FIG. 11.
Figure 17:
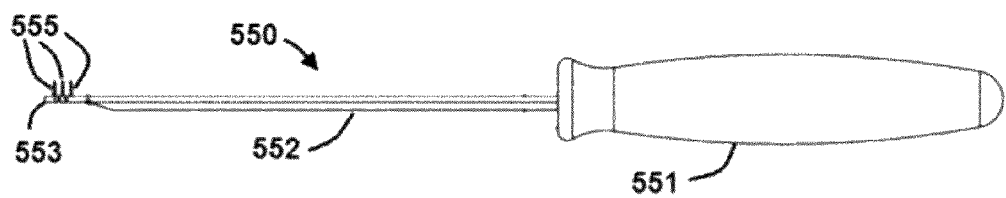
FIG. 17 is a top view of the insertion device of FIG. 11.
Figure 18:
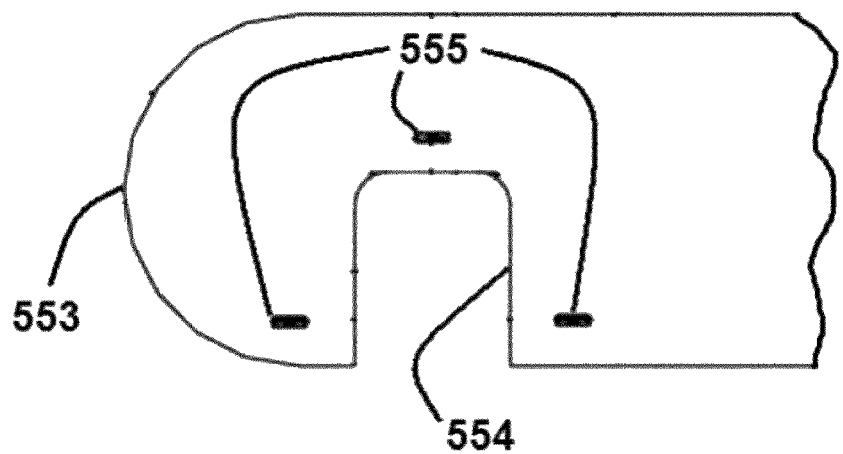
FIG. 18 is a detailed view of a portion of the insertion device of FIG. 11.
Figure 19:
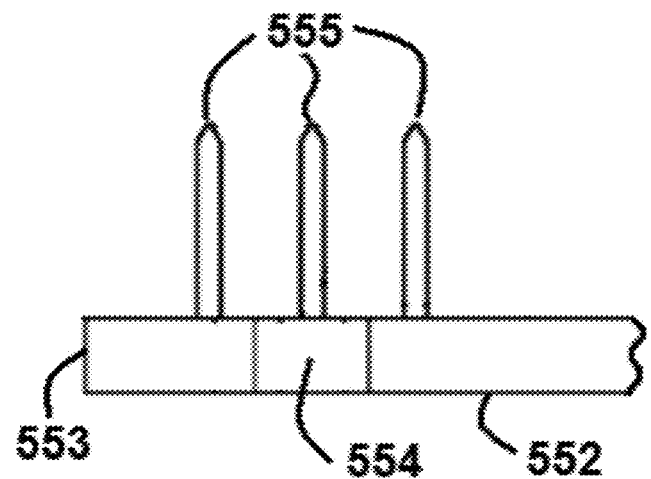
FIG. 19 is a detailed view of a portion of the insertion device of FIG. 11.
Figure 20:
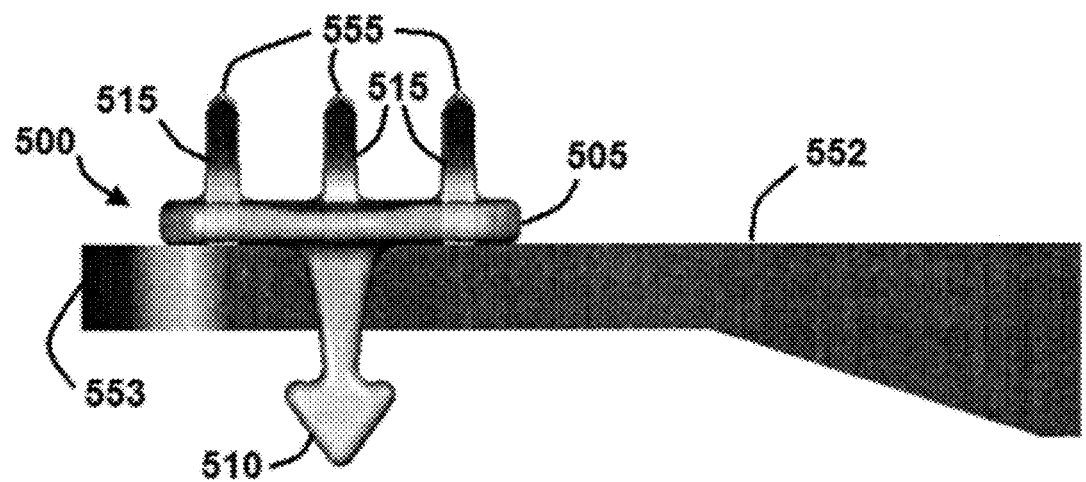
FIG. 20 is a detailed view of a portion of the implant and insertion device of FIG. 11.
Figure 21:
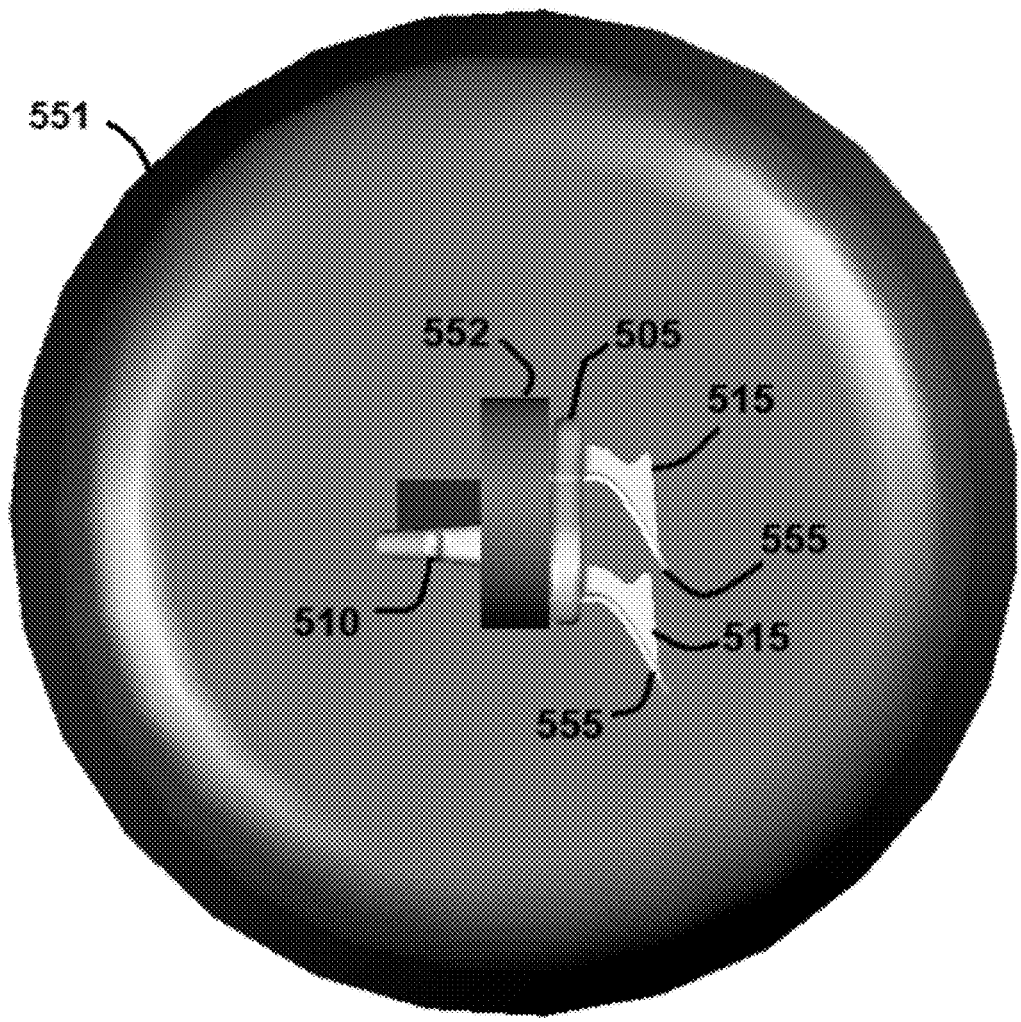
FIG. 21 is an end view of a portion of the implant and insertion device of FIG. 11.
Figure 22:
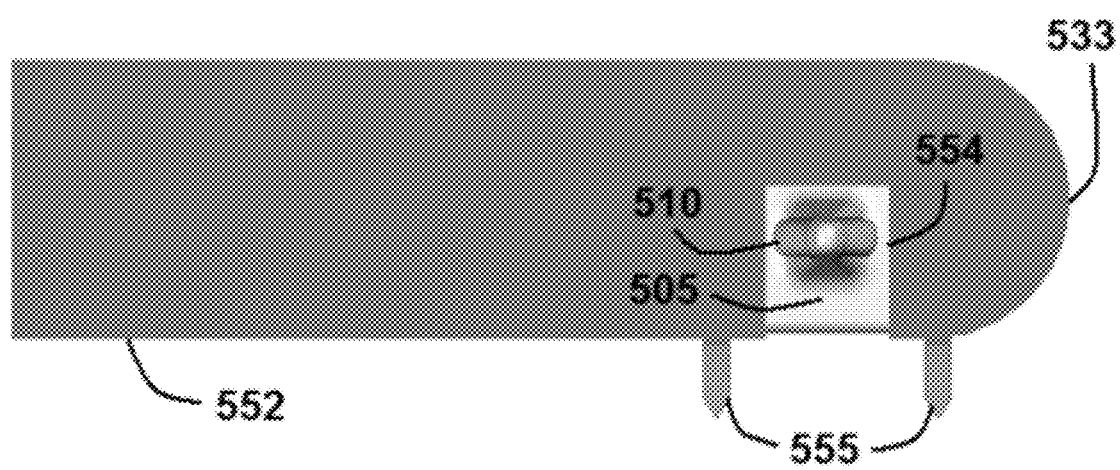
FIG. 22 is a detailed view of a portion of the implant and insertion device of FIG. 11.

Referring specifically now to FIGS. 16-19, insertion device 550 comprises a handle portion 551 and a shaft 552 with a distal end 553. Proximal to distal end 553 is a relief or recessed portion 554 and a plurality of projections or needles 555. It is understood that the term "needle" as used herein encompasses any sharp object configured to pierce tissue. Implant 500 and insertion device 550 are configured such that turbinate barb 510 will fit within relief portion 554 and needles 555 will extend through apertures 520 when implant 500 is coupled to insertion device 550. As shown in the embodiment of FIGS. 11 and 21, septum barbs 515 curve downward and deflect needles 555, which are flexible enough to elastically deform to the position shown in FIGS. 11 and 21. In other embodiments, needles 555 may be curved prior to engagement with septum barbs 515. In the end view of FIG. 21, it is possible to see that septum barbs 515 extend from one side of shaft 552, while turbinate barb 510 extends from the other side of shaft 552. Referring now to FIG. 22, turbinate barb 510 extends through relief portion 554. The lower portions of a pair of needles 555 are also visible in FIG. 22.

Figure 23A:
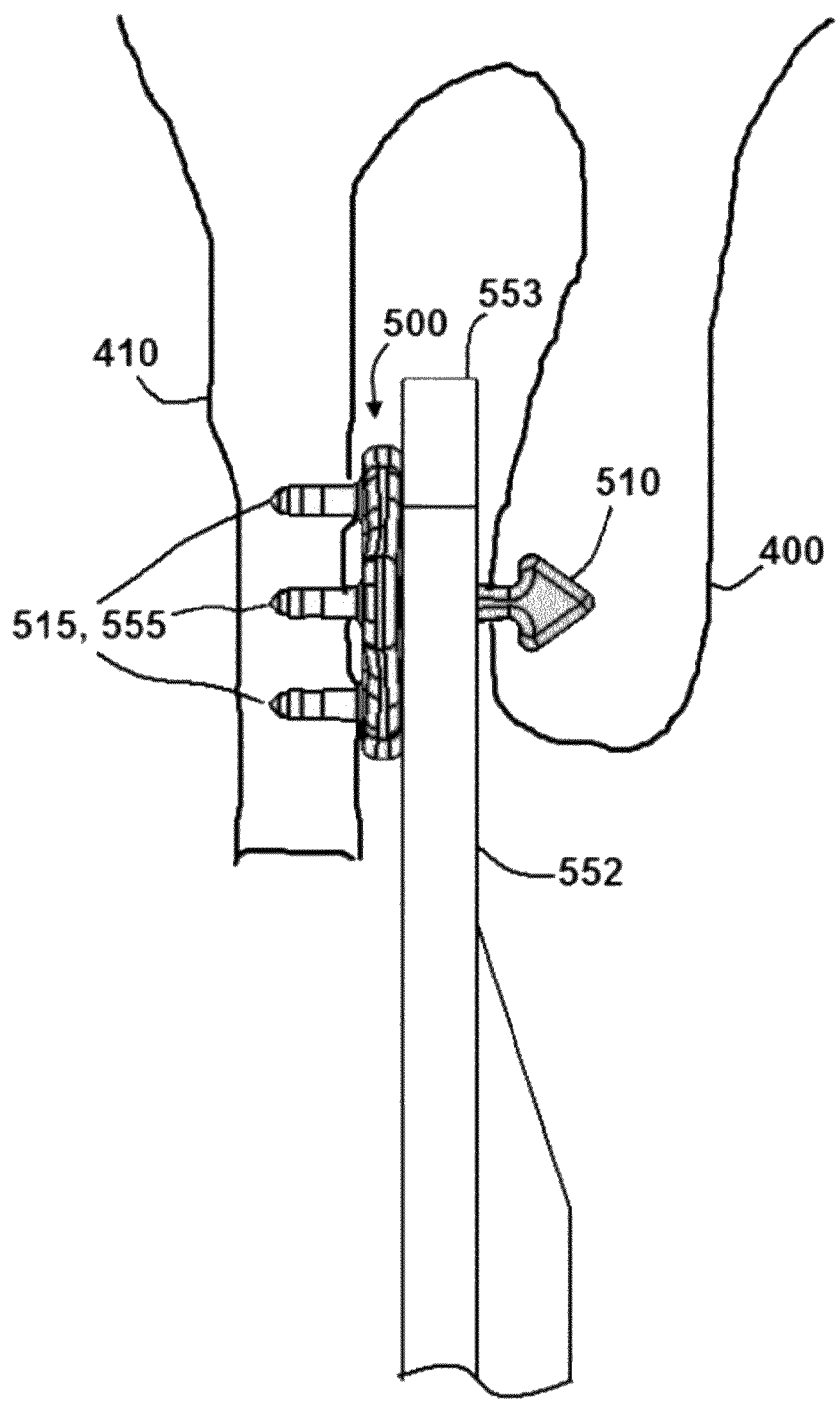
FIG. 23A is a partial section view of a portion of the implant and insertion device of FIG. 11 during a method of installation according to an exemplary embodiment of the present disclosure.

During installation according to one specific embodiment, a user may grasp the handle portion 551 of insertion device 550 and place distal end 553 and implant 500 into a patient's nasal cavity and between the turbinate and septum. As shown in FIG. 23, the user may then identify the adjacent nasal septal mucosa that is in proximity to the most anterior aspect of the turbinate 400 and place septum barbs 515 into the mucosa of the nasal septum 410, allowing turbinate barb 510 to be perpendicular to the anterior aspect of the turbinate 400. Needles 555 extend beyond the ends of septum barbs 515 and can lead septal barbs 515 into septum 410. After securing implant 500 in the septal mucosa, a user may push turbinate 400 medially until turbinate barb 510 pierces turbinate 400. The user may utilize a freer or other flat instrument (not shown) to push turbinate 400 medially. After turbinate 400 has been secured to turbinate barb 510, a user can remove insertion device 550 by rotating insertion device about its longitudinal axis. In the position shown in FIG. 23A, a user can rotate insertion device so that the top portion of shaft 552 is directed towards the right. This movement allows needles 555 to be withdrawn from septum 410, while leaving septal barbs 515 coupled to septum 410. Relief 554 provides clearance for turbinate barb 510 as shaft 552 is rotated. When needles 555 have been withdrawn from septum 410, insertion device 550 can be moved so that turbinate barb 510 is no longer located within recess 554. Insertion device 550 can then be withdrawn from the nasal cavity, leaving implant 500 in place.

In specific embodiments, implant 500 is configured to medialize the middle turbinate for one week allowing healing of the lateral nasal wall to take place. In specific exemplary embodiments, implant 500 may be comprised of a resorbable polylactide-co-glycolide biomaterial and may have the following approximate dimensions: 6.2 mm long, 4.7 mm wide and 7 mm thick. In certain embodiments, implant 500 can be configured to degrade within approximately 2-6 months.

Figure 23B:
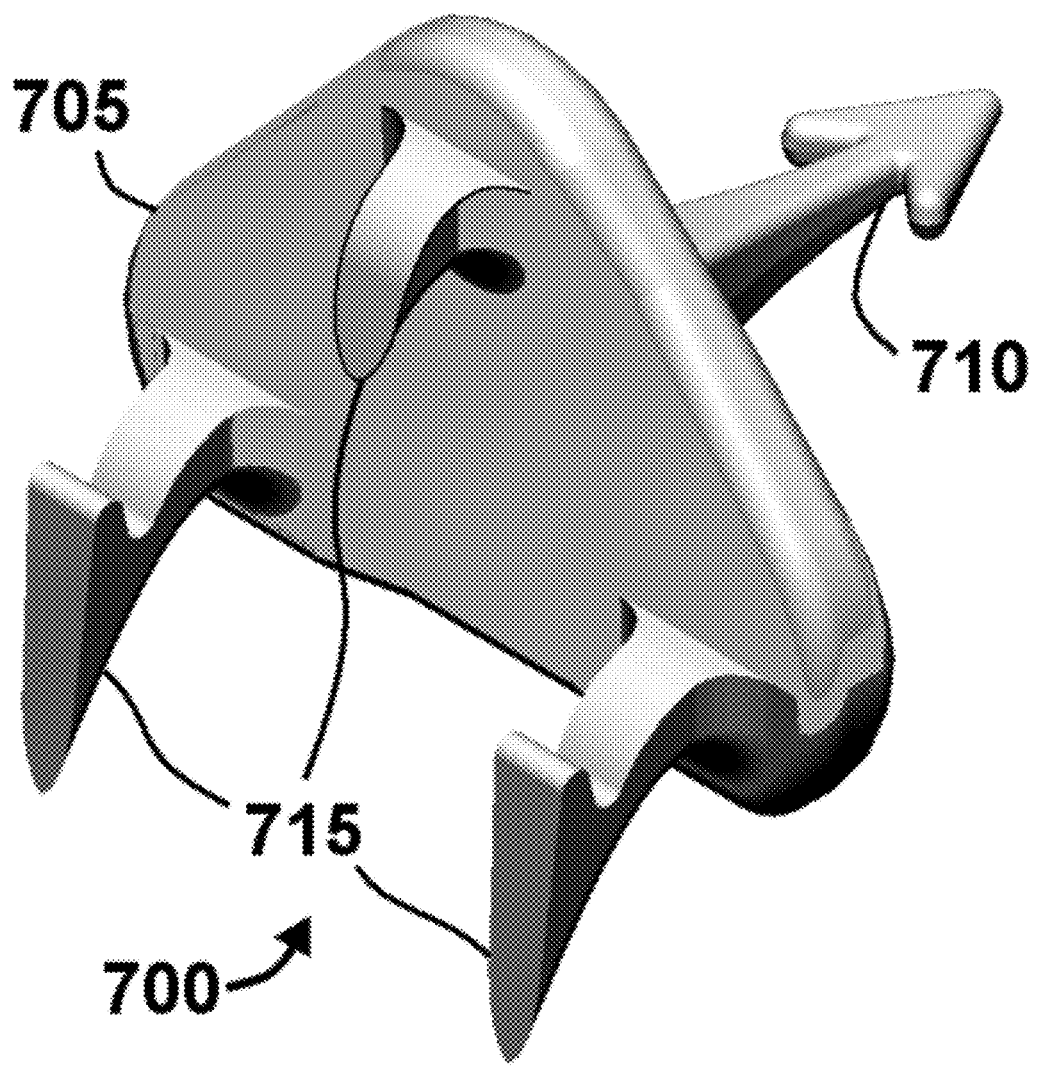
FIG. 23B is a perspective view of a another embodiment of an implant.

Referring now to FIG. 23B, another embodiment of an implant 700 is similar to the previously-described implant 500. This embodiment comprises a main body 700, a turbinate projection or barb 710, three septum projections or barbs 715, and three apertures (not visible in the view shown in FIG. 23B). This embodiment may also be installed using insertion device 550 in a manner similar to that described above for implant 500.

However, in this embodiment, the upper central septal barb 715 is slightly shorter than the other septal barbs 715 (e.g., the upper central barb 715 does not extend as far away from main body 700 as do the other septal barbs 715). During installation, the upper central septal barb 715 will not engage the tissue at the same time as the other two septal barbs 715. In certain embodiments, this can make it easier to install implant 700 into the desired tissue.

Figure 24:
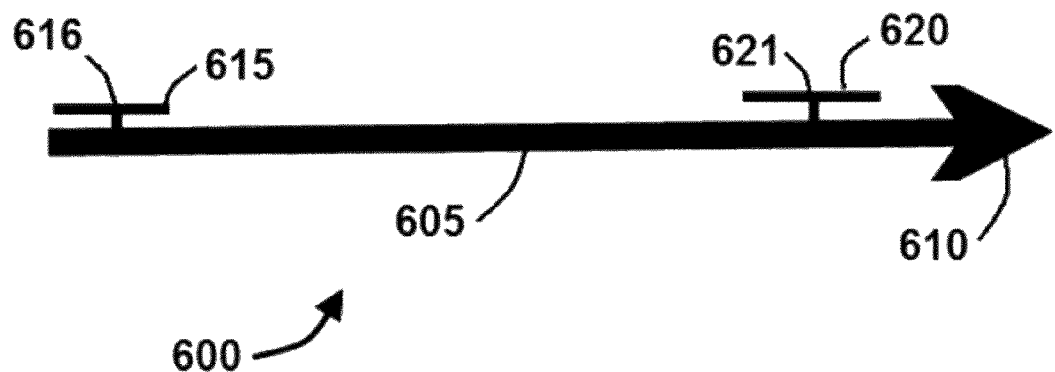
FIG. 24 is a side view of an implant according to an exemplary embodiment of the present disclosure.
Figure 25:
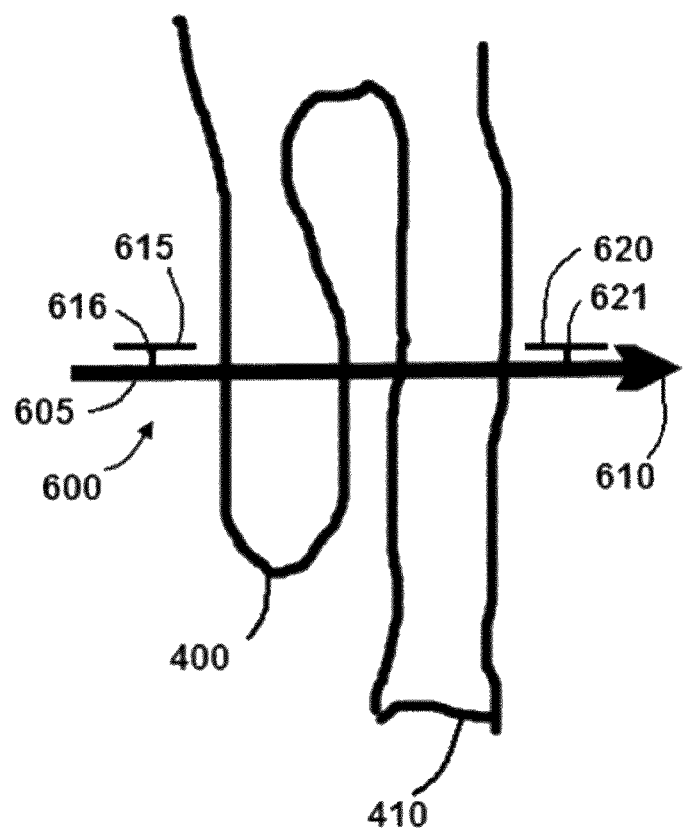
FIG. 25 is a partial section view of the implant of FIG. 24 during a method of installation according to an exemplary embodiment of the present disclosure.
Figure 26:
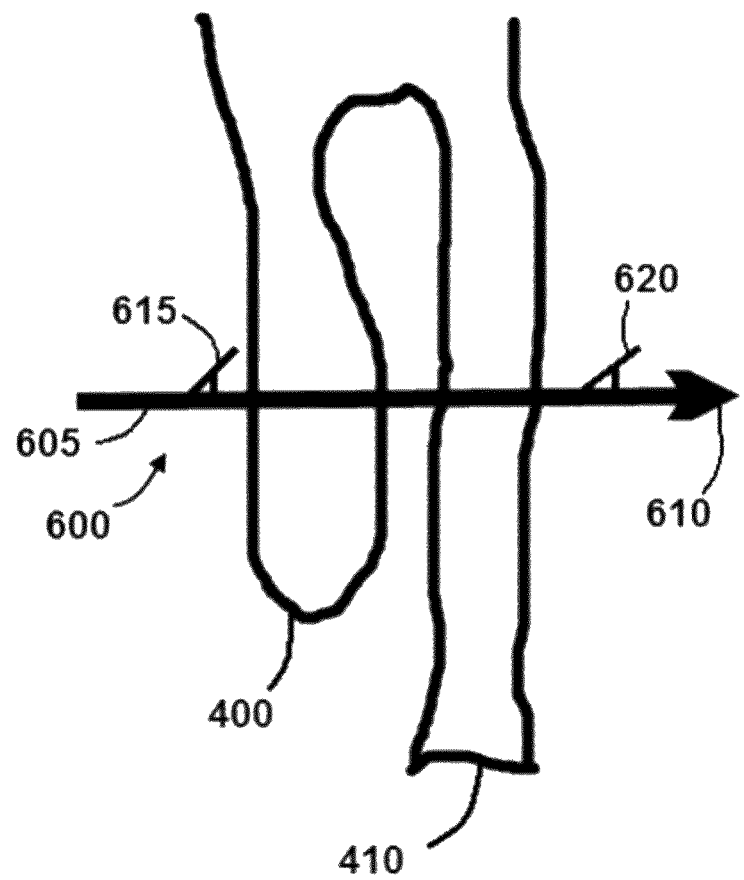
FIG. 26 is a partial section view of the implant of FIG. 24 during a method of installation according to an exemplary embodiment of the present disclosure.

Referring now to FIGS. 24-26, another embodiment of an implant 600 configured to medialize a turbinate to a septum comprises an elongate main body 605, a tapered end surface 610, and a pair of pivoting or locking members 615, 620 coupled to main body 605 via pivots 616, 621. It is understood that FIGS. 24-26 are not to scale and that locking members 615, 620 may be closer to main body 605 than shown in the figures. Certain dimensions of implant 600 may be altered in the figures to provide clarity.

In this embodiment, locking members 615 and 620 are initially positioned to be aligned with main body 605. With implant 600 in this configuration, it can penetrate turbinate 400 and septum 410. In this embodiment, implant 600 penetrates both turbinate 400 and septum 410 far enough so that locking member 620 is on the side of septum 410 that is opposite of turbinate 400. When implant 600 is so positioned, locking members 615 and 620 can be rotated into the position shown in FIG. 26. When locking members 615 and 620 are positioned as shown in FIG. 26, turbinate 400 can be held proximal to septum 410. It is understood that while rotating locking members are shown in this embodiment, other configurations for locking members may be used in other embodiments. For example, locking members that extend in length or extend from the main body of the implant may also be used.

Exemplary embodiments of implants described above can be made of any biocompatible material. In certain embodiments, the implant is made of a biodegradable material. In specific embodiments, the material is a biodegradable polymer. In certain embodiments, the material is a co-polymer. In certain embodiments, the polymer is a polyester, polyanhydride, polyamide, polycarbonates, polycarbamate, polyacrylate, polymethacrylate, polystyrene, polyurea, polyether, or polyamine. In certain embodiments, the polymer is a polyester such as poly(glycolide-co-lactide) (PLGA), polyglycolic acid, poly-β-hydroxybutyrate, and polyacrylic acid ester. In certain embodiments, the implant is made of PLGA. In certain particular embodiments, the implant is made of 65% D,L-lactide and 35% glycolide co-polymer. The polymer selected can be formable and able to degrade in-vivo without producing toxic side products. Biodegradable polymers known in the art are useful in embodiments of this invention.

Any of the inventive devices can be made of any biocompatible material. Preferably, the device is made of a biodegradable material. In certain embodiments, the material is a biodegradable polymer. The material may be synthetic (e.g., polyesters, polyanhydrides) or natural (e.g., proteins, rubber, polysaccharides). In certain embodiments, the material is a homopolymer. In certain embodiments, the material is a co-polymer. In still other embodiments, the material is a block polymer. In other embodiments, the material is a branched polymer. In other embodiments, the material is a cross-linked polymer. In certain embodiments, the polymer is a polyester, polyurethane, polyvinyl chloride, polyalkylene (e.g., polyethylene), polyolefin, polyanhydride, polyamide, polycarbonate, polycarbamate, polyacrylate, polymethacrylate, polystyrene, polyurea, polyether, polyphosphazene, poly (ortho esters), polycarbonate, polyfumarate, polyarylate, polystyrene, or polyamine. In certain embodiments, the polymer is polylactide, polyglycolide, polycaprolactone, polydioxanone, polytrimethylene carbonate, and co-polymers thereof. Polymers that have been used in producing biodegradable implants and are useful in preparing the inventive devices include alpha-polyhydroxy acids; polyglycolide (PGA); copolymers of polyglycolide such as glycolide/L-lactide copolymers (PGA/PLLA), glycolide/D,L-lactide copolymers (PGA/PDLLA), and glycolide/trimethylene carbonate copolymers (PGA/TMC); polylactides (PLA); stereocopolymers of PLA such as poly-L-lactide (PLLA), poly-D, L-lactide (PDLLA), L-lactide/D,L-lactide copolymers; copolymers of PLA such as lactide/tetramethylglycolide copolymers, lactide/trimethylene carbonate copolymers, lactide/.delta.-valerolactone copolymers, lactide .epsilon.-caprolactone copolymers, polydepsipeptides, PLA/polyethylene oxide copolymers, unsymmetrically 3,6-substituted poly-1,4-dioxane-2,5-diones; polyhydroxyalkanate polymers including poly-beta-hydroxybutyrate (PHBA), PHBA/beta-hydroxyvalerate copolymers (PHBA/HVA), and poly-beta-hydroxypropionate (PHPA); poly-p-dioxanone (PDS); poly-.delta.-valerolatone; poly-r-caprolactone; methylmethacrylate-N-vinyl pyrrolidone copolymers; polyesteramides; polyesters of oxalic acid; polydihydropyrans; polyalkyl-2-cyanoacrylates; polyurethanes (PU); polyvinyl alcohol (PVA); polypeptides; poly-beta-maleic acid (PMLA); poly (trimethylene carbonate); poly(ethylene oxide) (PEO); poly (.beta.-hydroxyvalerate) (PHVA); poly(ortho esters); tyrosine-derived polycarbonates; and poly-beta-alkanoic acids. In certain embodiments, the polymer is a polyester such as poly(glycolide-co-lactide) (PLGA), poly(lactide), poly(glycolide), poly(D,L-lactide-co-glycolide), poly(L-lactide-co-glycolide), poly-.beta.-hydroxybutyrate, and polyacrylic acid ester. In certain embodiments, the device is made of PLGA. In certain embodiments, the device is made of 85% D,L-lactide and 15% glycolide co-polymer. In certain embodiments, the device is made of 50% D,L-lactide and 50% glycolide co-polymer. In certain embodiments, the device is made of 65% D,L-lactide and 35% glycolide co-polymer. In certain embodiments, the device is made of 75% D,L-lactide and 25% glycolide co-polymer. In certain embodiments, the device is made of 85% L-lactide and 15% glycolide co-polymer. In certain embodiments, the device is made of 50% L-lactide and 50% glycolide co-polymer. In certain embodiments, the device is made of 65% L-lactide and 35% glycolide co-polymer. In certain embodiments, the device is made of 75% L-lactide and 25% glycolide co-polymer. In certain embodiments, the device is made of poly (caprolactone). In certain embodiments, the device is made of Pebax, Polyimide, Braided Polyimide, Nylon, PVC, Hytrel, HDPE, or PEEK. In certain embodiments, the device is made of a fluoropolymer such as PTFE, PFA, FEP, and EPTFE. In certain embodiments, the device is made of latex. In other embodiments, the device is made of silicone. The polymer typically has a molecular weight sufficient to be shaped by molding or extrusion. The device is typically made of a material that is bioabsorbed after the device is not longer needed. For example, the device may degrade after 1 week, 2 weeks, 3 weeks, 1 month, 2 months, 3 months, 4 months, 5 months, 6 months, 9 months, 1 year, 1.5 years, 2 years, 3 years, etc. The polymer used to make the device may be selected based on its degradation profile. The polymer can be selected as is known to the art to have a desired degradation period. For an implant of this invention, the degradation period is preferably up to about 2 years, or between about 3 weeks and about 1 year, or between about 6 weeks and about 3 months. As would be appreciated by one of skill in this art, the composition of the device may be varied to achieve the desired lifetime in vivo of the wafer.

Certain embodiments of the turbinate medializer include features such as hooks and barbs which need to be rigid and stiff enough to pierce and penetrate the mucosal or similar tissue. To function properly for the weeks after implantation, these hooks and barbs need to retain sufficient strength to approximate the body of the MTM close to the septum and turbinate. Furthermore, these features also need to be strong and somewhat elastic so that they do not easily fracture during the process of implantation. To achieve that property, the medializer may be composed of a crystalline or amorphous polymer combined with an elastomeric polymer. For example, a highly crystalline polylactide may be blended with a polyhydroxybutarate; specifically 80-97% PLLA and 20-3% PHA. Similarly, adding caprolactone or trimethyl carbonate may be added to the crystalline polymer to make it more elastic. Elasticity of the construct is achieved through the addition of the caprolactone or trimethyl carbonate to a lactide or glycolide monomer since the caprolactone and trimethyl carbonate have relatively low melting temperatures, i.e. −60° C. for carpolactone.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An implant configured to medialize a turbinate to a septum, the implant comprising:
   a triangular main body comprising a first substantially continuous triangular planar surface and a second substantially continuous triangular planar surface, the main body further comprising an inferior and a superior portion;
   a first barb, a second barb and a fourth barb extending from the first substantially continuous triangular planar surface and curving towards the inferior portion of the body, wherein the first and second barbs extend from the inferior portion of the main body and the fourth barb extends from the superior portion of the main body and is shorter than the first and second barbs; wherein the first, second and fourth barbs are configured so that during implant installation, the inferior portion and thereby the first and second barbs engage and penetrate the mucosa of a nasal septum, before the fourth barb engages and penetrates the nasal septum, thereby easing installation; and
   a third barb extending from the second substantially continuous triangular planar surface, wherein the third barb comprises a shaft terminating in an arrowhead shaped member with a tip which is configured to pierce a turbinate.

2. The implant of claim 1 wherein the first, second and fourth barbs are adapted to be inserted before the third barb pierces the turbinate.

3. The implant of claim 1 wherein the third barb extends perpendicular from the second side.

4. A kit for medializing a turbinate to a septum, the kit comprising:
   an implant configured to medialize a turbinate to a septum, the implant comprising:
      a main body comprising a first substantially planar side and a second substantially planar side, wherein the main body of the implant is triangular-shaped;
      a first barb, a second barb and a fourth barb extending from the first side, wherein the first and second barbs are curved as the first and second barbs extend from the first side of the main body and are configured to penetrate mucosa of a nasal septum;
      a first aperture adjacent the first barb, a second aperture proximal to the second barb and a third aperture proximal to the fourth barb;
      a third barb extending from the second side, wherein the third barb is configured to penetrate a turbinate; and
   an insertion device comprising a handle portion, a shaft, a distal end, and first, second, and third projections proximal to the distal end, wherein:
   the first projection is configured to extend through the first aperture, the second projection is configured to extend through the second aperture, and the third projection is configured to extend through the third aperture when the implant is coupled to the insertion device.

5. The kit of claim 4, wherein the first, second and third projections are flexible.

6. The kit of claim 4 wherein the insertion device comprises a recessed portion configured to engage the implant when the implant is coupled to the insertion device.

7. A method of medializing a turbinate, the method comprising:
   providing an implant comprising: a main body comprising a first substantially planar side and a second substantially planar side, wherein the main body of the implant is triangular-shaped;
      a first barb, a second barb and a fourth barb extending from the first side, wherein the first and second barbs are curved as the first and second barbs extend from the first side of the main body and are configured to penetrate mucosa of a nasal septum; and
      a third barb extending from the second side, wherein the third barb is configured to penetrate a turbinate; and
   providing a first aperture adjacent the first barb of the implant, a second aperture proximal to the second barb and a third aperture proximal to the fourth barb;
   providing an insertion device comprising a handle portion, a shaft, a distal end, and first, second, and third projections proximal to the distal end;
   inserting the first projection of the insertion device through the first aperture of the implant, the second projection of the insertion device through the second aperture of the implant, and the third projection of the insertion device through the third aperture of the implant;
   inserting the implant and the distal end of the insertion device into a nasal cavity between a turbinate and a septum;
   inserting the first barb into the septum;
   inserting the third barb into the turbinate;
   removing the first projection from the first aperture; and
   removing the insertion device from the nasal cavity.

8. The method of claim 7 wherein removing the first projection from the first aperture comprises rotating the insertion device about a longitudinal axis of the shaft of the insertion device.

9. The method of claim 7 wherein the insertion device comprises a recessed portion proximal to the distal end.

10. The method of claim 9 wherein the recessed portion is configured so that the third barb extends through the recessed portion when the first projection of the insertion device is inserted through the first aperture of the implant.

11. A method of medializing a turbinate, the method comprising:

provoking an implant comprising: a main body comprising a first substantially planar surface and a second substantially planar surface; an inferior side and a superior side;

a first, second and fourth curved barbs configured to penetrate mucosa of a nasal septum, extending from the first surface and curving towards the inferior side of the implant, wherein the first and second barbs extend further than the fourth barb from the first surface such that the fourth barb is shorter than the first and second barbs; and a third barb extending from the second surface, wherein the third barb is configured to penetrate a turbinate; and inserting the implant into a nasal cavity between a turbinate and a nasal septum;

orienting the first surface so that the first and second barbs engage an inferior portion of the nasal septum followed by inserting the first and second barbs into the nasal septum along a curved trajectory, the curves of the first and second barbs defining the trajectory;

moving the implant along the curved trajectory so that the fourth barb engages and penetrates a superior portion of the nasal septum after the first and second barbs are inserted into the nasal septum; and pushing the turbinate onto the third barb so that the third turbinate pierces and secures the turbinate once the first, second and fourth barbs fully extend into the nasal septum.

\* \* \* \* \*